United States Patent [19]

Han et al.

[11] Patent Number: 5,763,181
[45] Date of Patent: Jun. 9, 1998

[54] CONTINOUS FLUOROMETRIC ASSAY FOR DETECTING NUCLEIC ACID CLEAVAGE

[75] Inventors: Myun Ki Han, Silver Spring; S. Paul Lee, Phoenix; Jack G. Chirikjian, Potomac, all of Md.

[73] Assignee: Georgetown University, Washington, D.C.

[21] Appl. No.: 706,135

[22] Filed: Aug. 30, 1996

Related U.S. Application Data

[63] Continuation of Ser. No. 365,473, Dec. 30, 1994, abandoned.

[51] Int. Cl.$^6$ .............................. C12Q 1/68; C12P 19/34; C07H 21/04
[52] U.S. Cl. ............................... 435/6; 435/18; 435/91.2; 536/24.3
[58] Field of Search .................... 435/6, 18, 91.2; 536/24.3, 24.31, 24.32, 24.33, 23.1

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,683,202 | 7/1987 | Mullis et al. | 435/91 |
| 4,876,187 | 10/1989 | Duck et al. | 435/6 |
| 4,996,143 | 2/1991 | Heller et al. | 435/6 |
| 5,001,769 | 3/1991 | Duck et al. | 435/6 |

FOREIGN PATENT DOCUMENTS

| | | |
|---|---|---|
| WO 89/09284 | 10/1989 | WIPO. |
| WO 89/09835 | 10/1989 | WIPO. |

OTHER PUBLICATIONS

Gingeras et al, "A spectrofluorometric method for measurement of restriction endonuclease activity based on fluorescence polarization", J. Cell. Biochem. Suppl. 17 Part C, p. 173, abstract K304, Feb. 1992.

Glasner et al, "Fast quantitative assay of sequence-specific endonuclease activity based on DNA sequencer technology", Biol. Chem. Hoppe-Seyler 373:1223-1225. Dec. 1992.

Freifelder, Molecular Biology, Jones and Bartlett Publishers, Boston, Ma, page 138, 1983.

Suggs et al., Use of Synthetic Oligodeoxyribonucteotides for the Isolation of Specific Cloned DNA Sequences, in: *ICN-UCLA Symposium on Development of Biology Using Purified Genes*, Brown (ed.), Academic Press, Inc., New York (1981), pp. 683-693.

Telser et al., Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements, *J. Am. Chem. Soc. 111*:6966-76 (1989).

Terry et al., Properties of Avian Sarcoma-Leukosis Virus pp32-Related pOI-Endonucleases Produced in *Escherichia coli*, *J. Virol.* 62(7):2358-2365 (1988).

Varmus and Brown, "Retroviruses," in *Mobile DNA*, Berg, D.E. and Howe, M.M., eds., American Society for Microbiology. Washington, D.C. (1989), pp. 53-108.

Waters and Connolly, Continious Spectrophotometric Assay for Restriction Endonucleases Using Synthetic Oligodeoxynucleotides and Based on the Hyperchromic Effect, *Anal. Biochem* 204:204-209 (1992).

Wilson and Young, Isolation of a Sequence-specific Endonuclease (Bami) from *Bacillus amyloliquefaciens* H. *J. Mol. Biol.* 97:123-125 (1975).

Wu and Brand, Resonance Energy Transfer:Methods and Applications, *Anal. Biochem.* 218:1-13 (1994).

Ruth et al., Linker Arm Nucteotide Analogs Useful in Oligonucleotide Synthesis, *DNA* 4:93 (1985).

Ruth et al., DNA Affinity Supports Using Modified Oligonucleotide Attached to Nylon Membranes, Abstract 7088, *Fed. Proc.* 44:1622 (1985).

Rychlik and Rhoads, A computer program for choosing optimal oligonucleotide for filter hybridization, sequencing and in vitro amplification of DNA, *Nucleic Acids Res.* 17(21):8543-8551 (1989).

Schwartzberg et al., Construction and Analysis of Deletion Mutations in pol Gene of Moloney Murine Leukemia Virus:A New Viral Function Required for Productive Infection, *Cell* 37:1043-1052 (1984).

Sherman and Fyfe, Human immunodeficiency virus integration protein expressed in *Eschericia coli* possesses selective DNA cleaving activity, *Proc. Natl. Acad. Sci. USA* 87:5119-5123 (1990).

Smith et al., Analysis of Long Terminal Repeat Circle Junctions of Human Immunodeficiency Virus Type 1, *J. Virol* 64:6286-6290 (1990).

Spencer and Weber, Influence of Brownian Rotations and Energy Transfer upon the Measurements of Fluorescence Lifetime, *J. Chem. Phys.* 52(4):1654-1663 (1970).

Stryer, L., Fluorescence Energy Transfer As A Spectroscopic Ruler, *Ann. Rev. Biochem.* 47:819-846 (1978).

Stryer, L., Energy Transfer: A Spectroscopic Ruler, *Proc. Natl. Acad. Sci. USA* 58:719-726 (1967).

Jablonski et al., Preparation of oligodeoxynucleotide-alkaline phosphatase conjugates and their use as hybridization probes, *Nucleic Acids Res.* 14(15):6115-6128 (1986).

Jeltsch et al., A Fast and Accurate Enzyme-Linked Immunosorbent Assay for the Determination of the DNA Cleavage Activity of Restriction Endonucleases, *Anal. Biochem.* 213:234-240 (1993).

(List continued on next page.)

*Primary Examiner*—Stephanie W. Zitomer
*Assistant Examiner*—Jeffrey Fredman
*Attorney, Agent, or Firm*—Sterne, Kessler, Goldstein & Fox P.L.L.C.

[57] ABSTRACT

A method of detecting an enzyme-mediated DNA cleavage reaction in a fluorometric assay is provided. The method can be used to detect DNA cleavage caused by restriction endonucleases, retroviral integrase enzymes, DNases, RNases, or enzymes utilized in other strand separating processes in molecular biology.

15 Claims, 13 Drawing Sheets

OTHER PUBLICATIONS

Katz et al., Requirement for a conserved serine in both processing and joining activities of retroviral integrase, *Proc. Natl. Acad. Sci. USA 89*:6741–6745 (1992).

Katzman et al., The Avian Retroviral Integration Protein Cleaves the Terminal Sequences of Linear Viral DNA at the In Vivo Sites of Integration, *J. Virol. 63(12)*:5319–5327 (1989).

Knutson et al., Simultaneous Analysis of Multiple Fluorescence Decay Curves: A Global Approach, *Chem. Phys. Lett. 102(6)*:501–504 (1983).

Lee et al., A Fluorometric Assay for DNA Cleavage Reactions Characterized with BAMHI Restriction Endonuclease, *Anal. Biochem. 220*:377–383 (1994).

Matayoshi et al., Novel Fluorogenic Substrates for Assaying Retroviral Proteases by Resonance Energy Transfer, *Science 247*:954–957 (1990).

Murchie et al., Fluorescence energy transfer shows that the four–way DNA junction is a right-handed cross of antiparattel molecules, *Nature 341*:763–766 (1989).

Panganiban et al., The retrovirus pol gene encodes a product required for DNA integration: Identification of a retrovirus int locus, *Proc. Natl. Acad. Sci. USA 81*:7885–7889 (1984).

Connolly, B.A., The synthesis of oligonucleotide containing a primary amino group at the 5'-terminus, *Nucleic Acids Res. 15(7)*:3131–3137 (1987).

Conrad and Brand, Intramolecular Transfer of Excitation from Tryptophan to 1–Dimethylaminonaphthalene–5–sutfoamide in a Series of Model Compounds, *Biochemistry 7(2)*:777–787 (1968).

Cooper and Hagerman, Analysis of Fluorescence Energy Transfer in Duplex and Branced DNA Molecules, *Biochemistry 29*:9261–9268 (1990).

Craigie et al., The IN Protein of Moloney Murine Leukemia Virus Processes the Viral DNA Ends and Accomplishes Their Integration In Vitro, *Cell 62*:829–837 (1990).

Craigie et ad., A rapid in vitro assay for HIV DNA integration, *Nucleic Acids Res. 19(10)*:2729–2734 (1991).

Donehower et al., A mutant murine Leukemia virus with a single missense codon in pol is defective in a function affecting integration, *Proc. Natl. Acad. Sci. USA 81*:6461–6465 (1984).

Dreyer and Dervan, Sequence–specific cleavage of single stranded DNA:Oligodeoxynucleotide–EDTA Fe(II), *Proc. Natl. Acad. Sci. USA 82*:968–972 (1985).

Engelman et al., HIV–1 DNA Integration: Mechanism of Viral DNA Cleavage and DNA Strand Transfer, *Cell 67*:1211–1221 (1991).

Forster, T., Zwischenmolekulare Energiewanderung und FLuoreszenz, *Ann. Phys. (Leipzig) 2*:55–75 (1948).

Fujiwara et al., Retroviral DNA Integration: Structure of an Integration Intermediate, *Cell 54*:497–504 (1988).

Fujiwara et al., Integration of mini–retroviral DNA: A cell free reaction for biochemical analysis of retroviral integration, *Proc. Natl. Acad. Sci. USA 86*:3065–3069 (1989).

Ghosh et al., Real time kinetics of restriction endonuclease cleavage monitored by fluorescence resonance energy transfer, *Nucleic Acids Res. 22*:3155–3159 (1994).

Glazer et al., A stable double-stranded DNA–ethidium homodimer complex: Application to picogram fluorescence detection of DNA in agarose gels, *Proc. Nat. Acad. Sci. USA 87*:3851–55 (1990).

Grandgenett et al., Unraveling Retrovirus Integration, *Cell 60*:3–4 (1990).

Hippermeyer et al., Requirement of Avian Retrovirus pp32 DNA Binding Domain for Replication, *Virology 137*:358–370 (1984).

Beechem et al., Global And Target Analysis of Complex Decay Phenomena, *Anal. Instrum. 14(3&4)*:379–402 (1985).

Brown et ad , Retroviral integration: Structure of the initial covalent product and its precursor, and a role for the viral IN protein, *Proc. Natl. Acad. Sci. USA 86*:2525–2529 (1989).

Brumbaugh et al., Continuous, on–line DNA sequencing using oligodeoxynucleotide primers with multiple fluorophores, *Proc. Natl. Acad. Sci. USA 85*:5610–5614 (1988).

Bushman et al., Activities of human immunodeficiency virus (HIV) integration protein in vitro: Specific cleavage and integration of HIV DNA, *Proc. Natl. Acad. Sci. USA 88*:1339–1343 (1991).

Cardullo et al., Detection of nucleic acid hybridization by nonradioactive fluorescence resonance energy transfer, *Proc. Natl. Acad. Sci. USA 85*:8790–8794 (1988).

Carraway et al., Visualization of Epidermal Growth Factor (EGF) Receptor Aggregation in Plasma Membranes by Fluorescence Resonance Energy Transfer, *J. Biol. Chem. 264(15)*:8699–8707 (1989).

Chen and Scott, Special Review: Atlas of Ftuorescence Spectra and Lifetimes of Dyes Attached to Protein, *Anal. Lett. 18(A4)*:393–421 (1985).

Chollet and Kawashima, Biotin–Labeled synthetic oligoribonucleotides:chemical synthesis and uses as hybridization probes, *Nucleic Acids Res. 13(5)*:1529–1541 (1985).

Chow et al., Reversal of Integration and DNA Splicing Mediated by Integrase of Human Immunodeficiency Virus, *Science 255*:723–726 (1992).

Chu and Orgel, Laboratory Methods: Detection and Specific DNA Sequences with Short Biotin–Labeled Probes, *DNA 4(4)*:327–331 (1985).

Clavel et al., Genetic Recombination of Human Immunodeficiency Virus, *J. Virol. 63(3)*:1455–1459 (1989).

Clegg et al., Fluorescence Resonance Enery Transfer Analysis of the Structure of the Four–Way DNA Junction, *Biochemistry 31*:4846–4856 (1992).

Takahashi et al, (1991), "Use of a fluorescent DNA analog for fluorometric detection of DNAse activity", Anal. Biochem. 198:246–249.

Ofengand et al, (1973), "Use of photochemically induced cross–linking as a conformational probe of the tertiary structure of certain regions in transfer ribonucleic acid", Biochem. 32(10):1977–1984.

Lee et al, (1995), "Characterization of endonucleolytic activity of HIV–1 integrase using a fluorogenic substrate", Anal. Biochem. 227:295–301.

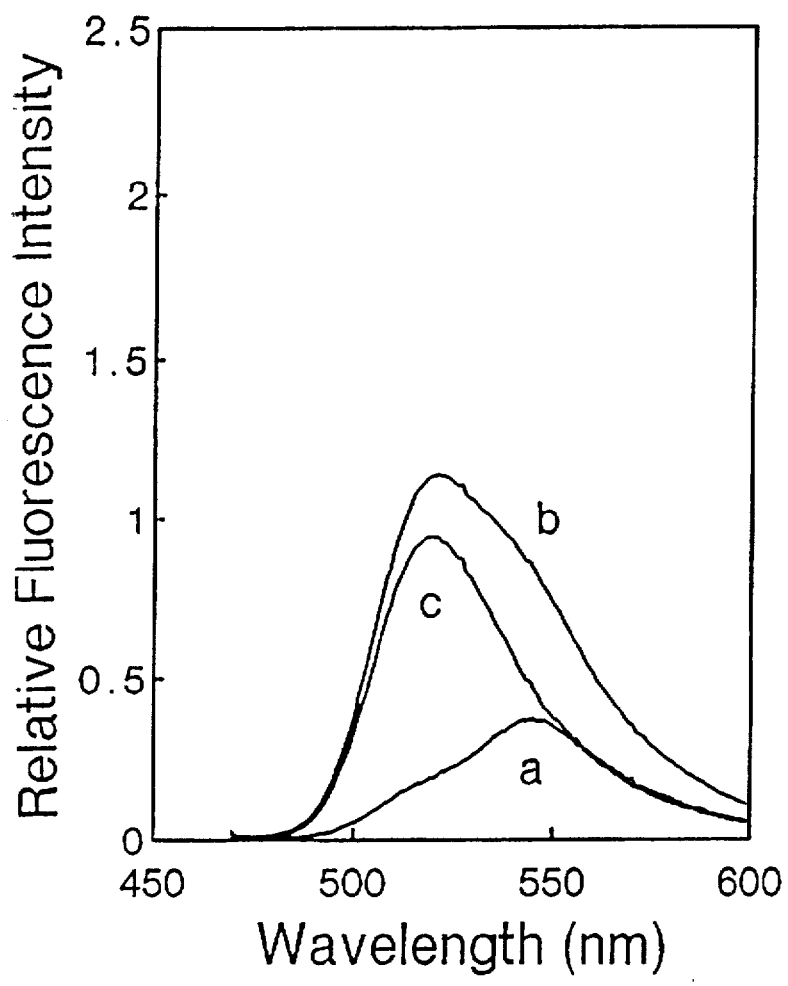
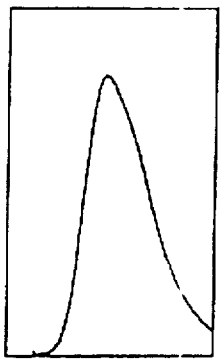
FIG. 9C
FIG. 9B

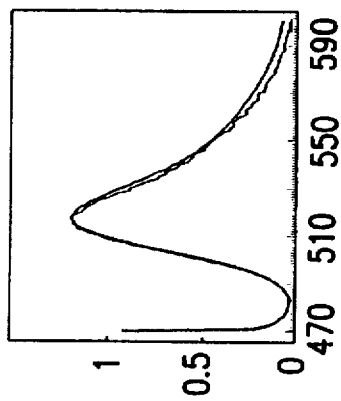
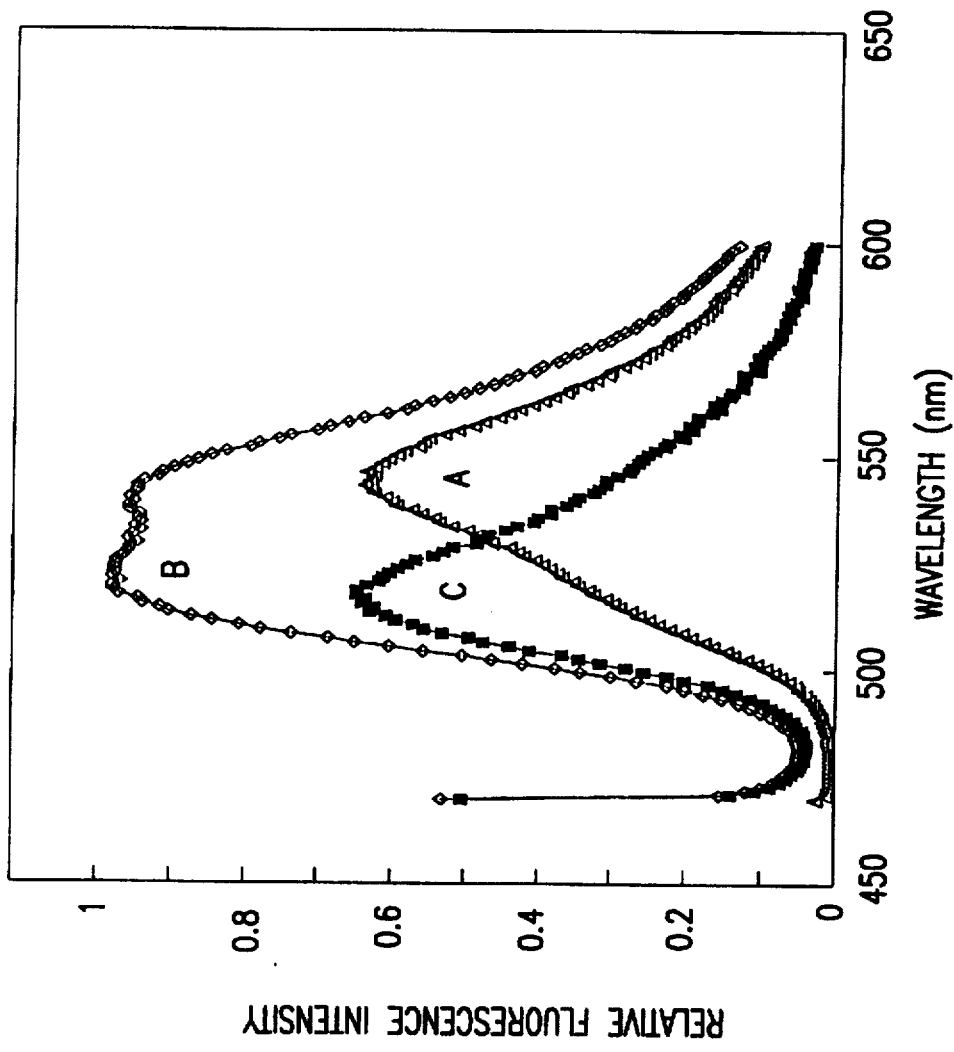
FIG. 10B
FIG. 10A

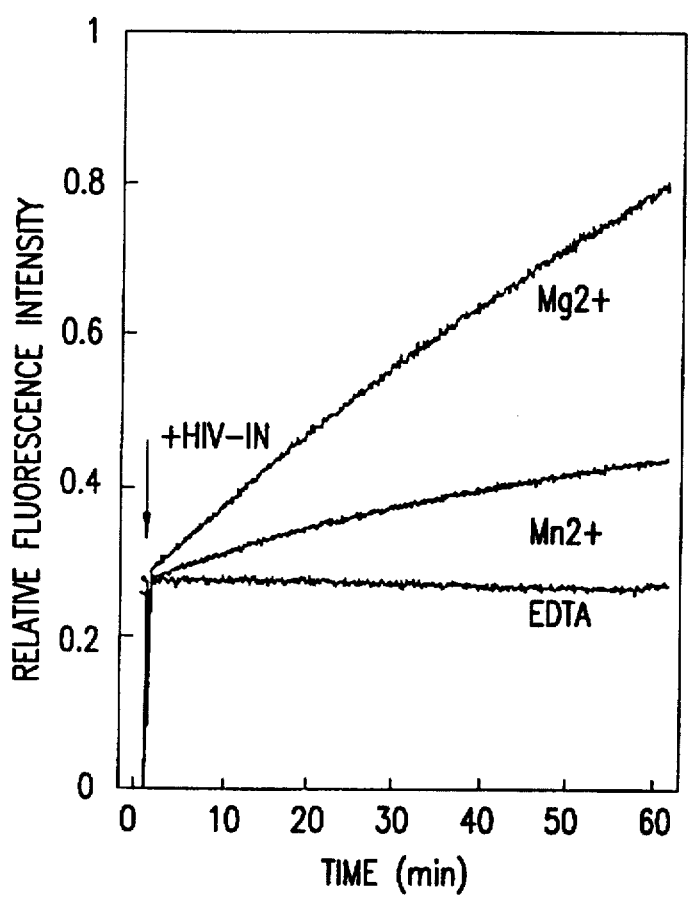
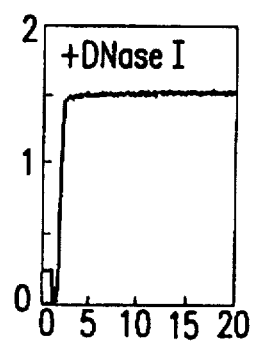
FIG. 11C
FIG. 11A

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: both ( i i ) MOLECULE TYPE:

( x i ) SEQUENCE DESCRIPTION: SEQ ID NO:1:

CCCCGGATCC ACCC                      1 4

( 2 ) INFORMATION FOR SEQ ID NO:2:

( i ) SEQUENCE CHARACTERISTICS:
    ( A ) LENGTH: 14 base pairs
    ( B ) TYPE: nucleic acid
    ( C ) STRANDEDNESS: both
    ( D ) TOPOLOGY: both ( i i ) MOLECULE TYPE:

( x i ) SEQUENCE DESCRIPTION: SEQ ID NO:2:

GGGGCCTAGG TGGG                                                                                  14

( 2 ) INFORMATION FOR SEQ ID NO:3:

( i ) SEQUENCE CHARACTERISTICS:
        ( A ) LENGTH: 49 base pairs
        ( B ) TYPE: nucleic acid
        ( C ) STRANDEDNESS: both
        ( D ) TOPOLOGY: both ( i i ) MOLECULE TYPE:

( x i ) SEQUENCE DESCRIPTION: SEQ ID NO:3:

TGAGTACCCG TGTGGAAAAT CTCTAGCAGG GNCTATGGCG TCCCCTCTG                                            49

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: both ( i i ) MOLECULE TYPE:

( x i ) SEQUENCE DESCRIPTION: SEQ ID NO:4:

ACTCATGGGC ACACCTTTTA GAGATCGTCA N                                                               31

( 2 ) INFORMATION FOR SEQ ID NO:5:

( i ) SEQUENCE CHARACTERISTICS:
        ( A ) LENGTH: 49 base pairs
        ( B ) TYPE: nucleic acid
        ( C ) STRANDEDNESS: both
        ( D ) TOPOLOGY: both ( i i ) MOLECULE TYPE:

( x i ) SEQUENCE DESCRIPTION: SEQ ID NO:5:

ACTCATGGGC ACACCTTTTA GAGATCGTCC CAGATACCGC AGGGGAGAC                                            49

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: both ( i i ) MOLECULE TYPE:

( x i ) SEQUENCE DESCRIPTION: SEQ ID NO:6:

GGGNCTATGG CGTCCCCTCT G                                                                          21

CONTINOUS FLUOROMETRIC ASSAY FOR DETECTING NUCLEIC ACID CLEAVAGE

This application is a continuation of application Ser. No. 08/365,473, filed Dec. 30, 1994 now abandoned.

BACKGROUND OF THE INVENTION

1. Field of the Invention

The present invention is in the fields of biochemistry and molecular biology. The invention relates to an assay for detecting nucleic acid cleavage reactions. More particularly, the invention relates to a continuous fluorometric assay for detecting nucleic acid cleavage reactions that are enzyme-mediated.

2. Description of the Related Art

Virtually all protocols in molecular biology require, at some point, cleavage of nucleic acids into smaller sized discrete fragments. In vitro cleavage of nucleic acids is typically accomplished with restriction endonucleases. Restriction endonucleases are commercially available enzymes, derived from bacteria, that recognize short DNA sequences and then cleave the double-stranded DNA at specific sites within, or adjacent to, the recognition sequence. These enzymes have been classified into three groups—Types I, II, and III. Type II restriction enzymes, which cleave a specific sequence of nucleotides and a separate methylase that modifies the same recognition sequence, are widely used in molecular cloning. A partial list of restriction enzymes and their recognition sequences is provided in Chapter 5 of Sambrook et al., *Molecular Cloning: A Laboratory Manual*, Cold Spring Harbor Laboratory Press, New York, (1989).

Restriction endonuclease cleavage of DNA into discrete fragments is one of the most basic procedures in molecular biology. The cleavage sites provide specific landmarks for obtaining a physical map of DNA. Further, the ability to produce specific DNA fragments by cleavage with restriction enzymes makes it possible to purify these fragments by molecular cloning. In addition, restriction enzymes have been utilized extensively for finding restriction fragment length polymorphisms (RFLPs) in allelic genomic regions. The use of RFLPs as genetic markers has been exploited in genetic linkage analysis, determination of patterns of inheritance for genetic disease, mapping of genes to specific chromosomal loci, and genetic fingerprinting.

Many enzymes other than restriction endonucleases are routinely used in molecular cloning. For example, DNases, RNases, exonucleases, and helicases are utilized in molecular biology to effect strand separation or denaturation of nucleic acids. These enzymes are discussed generally in Sambrook et al., *Molecular Cloning: A Laboratory Manual*, Cold Spring Harbor Laboratory Press, New York, (1989). Such enzymes are utilized in numerous processes in molecular biology that serve to amplify and detect DNA, such as, polymerase chain reaction (PCR) (described in U.S. Pat. Nos. 4,683,194, 4,683,195 and 4,683,202), ligase chain reaction (LCR) (described in published PCT application WO 89/09835), and catalytic hybridization amplification (CHA) (described in published PCT application WO 89/09284, and U.S. Pat. Nos. 5,011,769 and 4,876,187).

Ascertaining that nucleic acid cleavage has occurred, and evaluating the efficiency of the cleavage process, have traditionally been done using a gel electrophoresis assay system (Sambrook et al., supra). Such a system, however, is not only time-consuming and laborious, but the assay is discontinuous, meaning that the process cannot be monitored throughout the cleavage process. This is clearly a disadvantage in certain situations, such as where partial cleavage is desired, or where one needs to establish precise enzyme kinetic information. Further, the conventional assays are often inhibited by high concentrations of salt that may be required owing to the purification and solubility of the proteins involved. Finally, radioactive labeling of the substrates is often required to achieve the necessary level of sensitivity.

More recently, a continuous spectroscopic assay for endonucleases has been reported (Waters and Connolly, *Anal. Biochem* 204:204-209 (1992)). This assay is based on the hyperchromic effect resulting from turnover of a duplex oligonucleotide substrate to single-stranded DNA products. Although this technique is continuous, its scope is limited by its narrow dynamic range and limited range of substrate concentrations.

A sensitive non-isotopic enzyme linked immunoabsorbent assay (ELISA) for determining the DNA cleavage activity of restriction endonucleases was described by Jeltsch et al., *Anal. Biochem.* 213:234-240 (1993). This assay utilized DNA substrates that are labeled on both ends; one 5' end is labeled with biotin, and the other 5' end is labeled with fluorescein or digoxigenin. The use of biotin-labeled DNA in this assay renders the method discontinuous and necessitates extensive sample handling for the detection step.

Finally, endonuclease-catalyzed cleavage reactions of fluorophore-labeled oligonucleotides have been monitored by fluorescence resonance energy transfer (FRET) techniques (Ghosh et al., *Nucleic Acids Res.* 22:3155-3159 (1994)).

Fluorescence resonance energy transfer (FRET) (Forster, T., *Ann. Phys. (Leipzig)* 2:55-75 (1948); Stryer, L., *Annu. Rev. Biochem.* 47:819-846 (1978); Stryer, L., *Proc. Natl. Acad. Sci. USA* 58:719-726 (1967); Conrad and Brand, *Biochemistry* 7:777-787 (1968); Chen and Scott, *Anal. Lett.* 18:393 (1985); Wu and Brand, *Anal. Biochem.* 218:1-13 (1994)) is the transfer of electronic excitation energy by the Forster mechanism, and measures the distance between a pair of fluorophores (donor and acceptor) in macromolecules, in the range of 10-80 Angstroms (Å). Cardullo et al., *Proc. Natl. Acad. Sci. USA* 85:8790-8794 (1988), utilized FRET experiments to study the hybridization of complementary oligodeoxynucleotides. Upon hybridization, energy transfer was detected by both a decrease in fluorescein (donor) emission intensity and an enhancement of rhodamine (acceptor) emission. Cooper and Hagerman, *Biochemistry* 29:9261-9268 (1990), also utilized FRET to determine the interarm angles of a synthetic DNA four-way junction. However, these investigators reported that upon annealing of a fluorescent-modified strand and its unlabeled complementary strand, the probe fluorescence was quenched (Clegg et al., *Biochemistry* 31:4846-4856 (1992); Cooper and Hagerman, supra), and the wavelength of the emission spectrum was shifted upon the formation of duplex DNA. These results suggest that effects other than dipolar energy transfer mechanisms alter the donor fluorescence (in the presence or absence of acceptor at the ends of complementary strands), and that these effects must be examined in order to reliably measure distances in DNA molecules by FRET. Thus, the occurrence of nondipolar effects on fluorescently labeled DNA may distort the distances quantified by FRET in certain instances.

Thus, there exists a need in the art for a continuous, accurate, sensitive, and non-isotopic assay for detecting restriction enzyme mediated cleavage of nucleic acids.

Another class of enzymes that catalyze nucleic acid cleavage reactions are retroviral integrases. These enzymes are responsible for catalyzing the integration of viral DNA into the host organism's chromosomal DNA. Currently, the target of viral therapeutics is to screen compounds that inhibit these enzymes.

For example, one focus of AIDS research is to find specific inhibitors of each step in the replication cycle of the HIV retrovirus. Although progress has been made in targeting reverse transcription, parallel efforts in inhibiting other processes could lead to the development of new therapeutic agents. Retroviral integration is a particularly attractive target in the search for specific inhibitors due to the absence of any known cellular counterparts in the host. The combined use of antiviral drugs with different target specificities will facilitate the search for therapeutic intervention.

The currently established in vitro assay system for HIV DNA integration is based upon the detection of labeled $^{32}P$ integrated products either by electrophoresis or by biotin-avidin interaction (the substrate DNA being radiolabeled with $^{32}P$ at the 5' end and biotin at the 3' end). (Craigie et al., Nucleic Acids Res. 19:2729–2734 (1991)). Unfortunately, these methods are time consuming and often do not yield precise kinetic information. A sensitive and more rapid assay is desired in order to screen vast numbers of potential drugs and natural products. A rapid, sensitive, and continuous in vitro assay for screening the vast number of potential enzyme inhibitors is clearly needed to provide precise kinetic information necessary to determine the relative effectiveness of any inhibitor. Also, an assay is needed that would not be affected by high salt concentrations.

Thus, in light of the foregoing, there exists a need in the art for a continuous assay for accurately and sensitively detecting enzyme-mediated nucleic acid cleavage in vitro.

SUMMARY OF THE INVENTION

The present invention overcomes disadvantages of the prior art by providing a method of detecting an enzyme-mediated nucleic acid cleavage reaction in a continuous fluorometric assay comprising the steps of: a) preparing a fluorescently labeled oligonucleotide containing a nucleotide sequence recognizable by said enzyme, wherein said oligonucleotide acts as an enzyme substrate; (b) contacting said oligonucleotide of step a) with said enzyme in an amount sufficient to enzymatically cleave said oligonucleotide; and c) detecting a nucleic acid cleavage reaction by detecting an increase in fluorescence.

The invention also provides specific embodiments wherein the oligonucleotide is fluorescently labeled at one or both ends.

The invention also provides specific embodiments wherein the method of detecting an enzyme-mediated nucleic acid cleavage reaction is employed in a catalytic hybridization amplification procedure, or a polymerase or ligase chain reaction.

The invention also provides preferred embodiments wherein the nucleic acid cleavage reaction is mediated by a restriction enzyme, DNase, RNase, or retroviral integrase enzyme.

It is to be understood that both the foregoing general description and the following detailed description are exemplary and explanatory and are intended to provide further explanation of the invention as claimed.

For brevity, the following abbreviations are used throughout this application. FITC, fluorescein-5-isothiocyanate; EITC, eosin isothiocyanate; BamHI, restriction endonuclease derived from Bacillus amyloliquefaciens H; DNase I, Deoxyribonuclease I; HIV-1, human immunodeficiency virus type 1; IN, integrase (integration protein); EDTA, ethylenediaminetetraacetic acid; FRET, fluorescence resonance energy transfer; HPLC, high-performance liquid chromatography; DMF, dimethylformamide; 1,8-ANS, 1-anilinonaphthalene-8-sulfonic acid; DAS, decay associated spectra; PAGE, polyacrylamide gel electrophoresis.

BRIEF DESCRIPTION OF THE FIGURES

FIG. 2A is a graph depicting the DAS of the FITC-labeled single-strand oligonucleotide (0.27 µM).

FIG. 2B is a graph depicting the DAS of the FITC-labeled oligonucleotide (0.27 µM) annealed with its unlabeled complementary strand (0.4 µM). Both experiments were performed in 50 mM Tris, pH 8.0, 10 mM $MgCl_2$, and 0.1M NaCl at 25° C.

FIG. 3A is a graph depicting the emission spectra of FITC-labeled DNA substrates in the presence and absence of BamHI endonuclease at 25° C.

FIG. 3B is a graph depicting the emission spectra of FITC-labeled DNA substrates in the presence and absence of BamHI endonuclease at 37° C. Identical concentrations of annealed oligonucleotides (FITC-labeled and unlabeled complementary strand) were cleaved with the BamHI restriction endonuclease in 50 mM Tris, pH 8.0, 10 mM $MgCl_2$, and 0.1M NaCl and the emission spectra were recorded with an excitation wavelength at 490 nm. The spectra of the initial annealed oligonucleotides (top curve) and the enhanced fluorescence following cleavage (bottom curve) are shown.

FIG. 6A is a graph depicting the enzyme concentration-dependent BamHI cleavage of FITC-labeled DNA substrates. Curves A through D represent the kinetics of DNA cleavage by 10, 20, 40, and 60 units of BamHI, respectively. The kinetic experiments were performed with 0.5 µM DNA substrate in 420 µl of 50 mM Tris, pH 8.0, 10 mM $MgCl_2$, and 0.1M NaCl at 37° C. Fluorescence intensity was monitored with excitation and emission wavelengths of 520 nm and 490 nm, respectively. FIG. 6B shows the initial velocities of cleavage reactions determined from the linear portions of the kinetic data and plotted as a function of enzyme concentrations.

FIG. 7A is a graph depicting a BamHI cleavage reaction as a function of DNA substrate concentration. The graph shows a fluorometric analysis of the kinetics of a BamHI cleavage reaction (10 units in 100 µl of 50 mM Tris, pH 8.0, 10 mM MgCl$_2$, and 0.1M NaCl at 37° C). Curves A through E represent DNA cleavage reactions with 0.21, 0.36, 0.72, 1.08, and 0.18 µM DNA substrates, respectively. Curve E depicts the cleavage reaction in the presence of 25 mM EDTA. Each reaction was stopped after 11 minutes by the addition of 25 mM EDTA.

FIG. 7B is a photograph of the same reaction mixtures described in FIG. 7A, run on 20% PAGE. The photograph was taken under ultraviolet illumination using a Kodak green filter without ethidium bromide staining.

FIGS. 9A and 9B: FIG. 9A is a graph depicting steady-state emission spectra of a fluorogenic substrate in the presence and absence of DNase I, in the presence of $Mg^{2+}$. Curve a depicts the emission spectrum of 4 pmol of a fluorogenic substrate in 400 µl reaction buffer containing 25 mM HEPES, pH 7.5, 50 mM NaCl, 2 mM DTT, and 5% glycerol at 37° C. Curve b depicts the emission spectrum of the same substrate digested with DNase I. Curve c depicts the difference emission spectrum of curve b and curve a. Emission spectra were recorded with an excitation wavelength at 460 nm.

FIG. 9B is a graph depicting steady-state emission spectra of a fluorogenic substrate in the presence and absence of DNase I, in the presence of $Mn^{2+}$. Curves a–c are the same as described for FIG. 9A. Emission spectra were recorded with an excitation wavelength at 4460 nm. FIG. 9C shows peak normalized emission spectra of DNase I digested fluorogenic substrate in the presence of $Mg^{2+}$ and $Mn^{2+}$.

FIGS. 10A and 10B; FIG. 10A is a graph depicting steady-state emission spectra of a fluorogenic substrate in the presence and absence of HIV-IN. Curve A depicts the emission spectrum of 4 pmol of fluorogenic substrate in 400 µl reaction buffer containing 25 mM HEPES, pH 7.5, 50 mM NaCl, 2 mM DTT, and 5% glycerol at 37° C. Curve B depicts the emission spectrum of the same substrate digested with 40 pmol HIV-IN for 1 hour. Curve C depicts the difference emission spectrum of curve B and curve A. Emission spectra were recorded with an excitation wavelength at 460 nm. FIG. 10B shows peak normalized emission spectra of F-D1/T1 and the difference spectrum (curve C).

FIGS. 11A, 11B, and 11C: FIG. 11A is a graph depicting the kinetics of an HIV-IN cleavage reaction of a fluorogenic substrate monitored by FRET. The DNA cleavage reaction was initiated by the addition of HIV-IN to a preincubated reaction mixture containing 4 pmol of substrate. The conditions for the reactions are the same as in FIG. 10. Changes in fluorescence intensity were monitored with excitation and emission wavelengths of 460 and 510 nm, respectively. $Mn^{2+}$ quenched the fluorescence intensity of the substrate in the absence of the enzyme; thus, the kinetic data presented in this figure were intensity normalized according to the intensity ratio of the substrate in the presence of $Mg^{2+}$ and in the presence of $Mn^{2+}$.

FIG. 11B depicts the kinetics of an HIV-IN cleavage reaction of a fluorogenic substrate monitored by denaturing polyacrylamide gel electrophoresis (PAGE). The time course of a $^{32}$P-5'-labeled fluorescent substrate was determined by radiographic assays. Two reactions in parallel with 0.15 pmol substrate were reacted with 4 pmol HIV-IN in 15 µl reaction buffer at 37° C. The reactions were stopped at 1', 2.5', 5', 10', 15', 30' and 60' by addition of equal volume of stop solution. Reaction mixtures were analyzed by denaturing gel electrophoresis. Results were quantitated by utilizing a Hewlet-Packard ScanJet IIp and the densitometry program Scan Analysis 68020 (BioSoft). The line indicates the mean of the two experiments bounded by the actual values.

FIG. 11C depicts the kinetics of a DNaseI cleavage reaction.

DETAILED DESCRIPTION OF THE PREFERRED EMBODIMENTS

Figure 1:
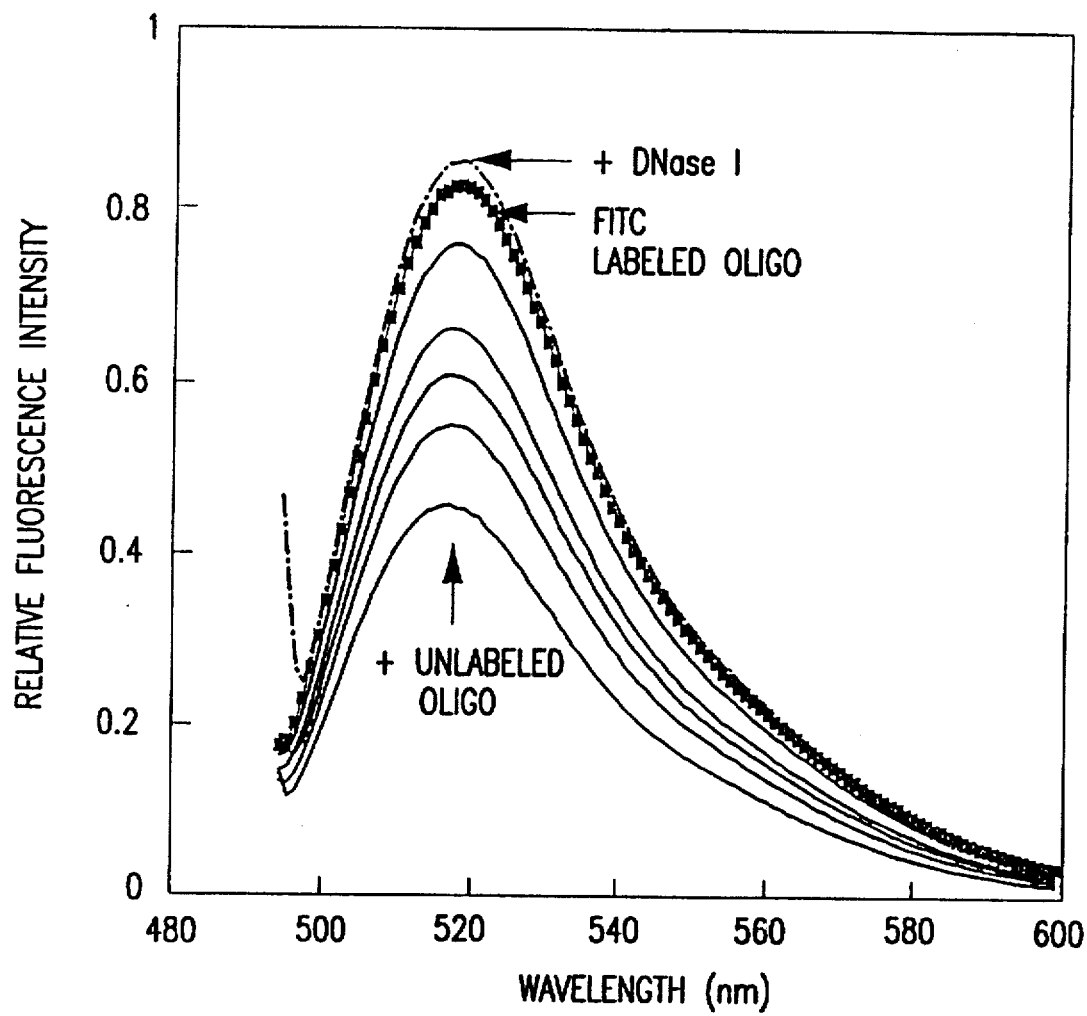
FIG. 1 is a graph depicting the fluorescence emission spectra of an FITC-labeled oligonucleotide. Changes in fluorescence intensity were recorded due to varying degrees of annealing of a 14-mer FITC-labeled oligonucleotide with its unlabeled complementary strands. Fixed concentrations (0.137 pmol) of the FITC-labeled oligonucleotide were annealed with 0.03 pmol, 0.06 pmol, 0.09 pmol, 0.117 pmol, and 0.15 pmol of the unlabeled complementary strand in 0.5 mL reaction volumes and their fluorescence intensities compared. Excitation wavelength was 490 nm.

The present invention is directed to a method of detecting an enzyme-mediated nucleic acid cleavage reaction using a continuous fluorometric assay. Generally, the present method employs a fluorescently-labeled oligonucleotide substrate containing a nucleotide sequence that is recognizable by the enzyme that will catalyze the cleavage reaction. For example, in the case of a restriction enzyme, the oligonucleotide will contain the restriction site recognized by that restriction enzyme.

The oligonucleotide substrate can be DNA or RNA, and may be single or double-stranded. The oligonucleotide can be labeled with a single fluorescent label or with a fluorescent pair (donor and acceptor) on a single-strand of DNA or RNA. The choice of single or double label will depend on the efficiency of the enzyme employed in the method of the invention. For example, a single fluorescent label can best be used with an efficient enzyme such as a restriction endonuclease.

In the method of the invention, there is no limitation on the length of the oligonucleotide substrate, so long as the fluorescent probe is labeled 6–7 nucleotides away from the enzyme cleavage site.

The term "fluorescent label" or "fluorophore" as used herein refers to a substance or portion thereof that is capable of exhibiting fluorescence in the detectable range. Examples of fluorophores that can be used according to the invention include fluorescein isothiocyanate, fluorescein amine, eosin, rhodamine, dansyl, and umbelliferone. Other fluorescent labels will be known to the skilled artisan.

Some general guidance for designing sensitive fluorescent labelled polynucleotide probes can be found in Heller and Jablonski's U.S. Pat. No. 4,996,143. This patent discusses the parameters that should be considered when designing fluorescent probes, such as the spacing of the fluorescent moieties (i.e., when a pair of fluorescent labels is utilized in the present method), and the length of the linker arms connecting the fluorescent moieties to the base units of the oligonucleotide. The term "linker arm" as used herein is defined as the distance in Angstroms from the purine or pyrimidine base to which the inner end is connected to the fluorophore at its outer end.

Preferably, in the method of the present invention, the donor and acceptor fluorophores should be attached to the oligonucleotide at positions which give them a relative separation of zero to twenty base units. The preferred separation is from zero to seven base units. The preferred length of the linker arm is a 12 carbon chain.

The term "cleavage that is enzyme-mediated" refers to cleavage of DNA or RNA that is catalyzed by such enzymes as DNases, RNases, helicases, exonucleases, restriction endonucleases, or retroviral integrases. Other enzymes that effect nucleic acid cleavage will be known to the skilled artisan and can be employed in the practice of the present invention. A general review of these enzymes can be found in Chapter 5 of Sambrook et al, supra.

Fluorescently labeled oligonucleotides and DNA fragments have been utilized in nucleic acid research, with applications that include DNA hybridization, automated DNA sequencing, fluorescence anisotropy, and resonance energy transfer studies. Past concerns with fluorescent-labeled DNA arose from interactions between fluorophores and DNA that result in quenched fluorescence. This quenching phenomenon is most problematic in FRET studies because quenching of the donor fluorescence could result from either resonance energy transfer or non-transfer effects.

In the first embodiment of the method of the present invention, cleavage of a single fluorescently labeled oligonucleotide substrate bearing the BamHI restriction site, was examined using the enzyme DNase I and the restriction endonuclease BamHI. Relief of non-transfer quenching of a 14-mer FITC-labeled oligonucleotide was characterized with both steady-state and time-resolved fluorescence techniques. The FITC-labeled single-strand was best fit by a triexponential decay with lifetimes of 0.5, 2.7, and 4.2 ns. The 4.2 ns component was found to contribute more than 80% of the total steady-state intensity. Upon annealing with an unmodified complementary strand, the contribution from the 4.2 ns component was significantly decreased, resulting in two-fold quenching of total fluorescence. The inventors reasoned that this quenching phenomenon should be a reversible process and, therefore, could be employed to study the numerous strand separation processes in molecular biology. The results demonstrated that the quenched fluorescence is totally recovered upon cleavage (compared to that of the single-strand). The extent of cleavage measured by fluorescence was confirmed by non-denaturing polyacrylamide gel electrophoresis analysis. This fluorescence "dequenching" technique can be used to quantify the kinetics of other restriction endonucleases, as well as other DNA strand separation and cleavage processes known to those skilled in molecular biology. It is also expected that the converse principal (decreased fluorescence) can be applied to methods in molecular biology involving nucleic acid ligation, as opposed to cleavage.

In the method of the present invention, chemical modifications of oligonucleotides and DNA fragments are easily accomplished by known methods using nucleotide analogs (Ruth et al., *DNA* 4:93 (1985); Telser et al., *J. Am. Chem. Soc.* 111:6966 (1989)) and DNA synthesis reagents. Phosphoramidites containing aliphatic primary amines may be introduced into the oligonucleotides at desired positions through automated DNA synthesizers. For example, Aminolink 2 (Applied Biosystems) and amino-modified-dT (Glen Research) can be used to introduce an aliphatic primary amine with a six-carbon linker at the 5'-end of oligonucleotides. This amine can react with a variety of substrates such as biotin (Chu and Orgel, *DNA* 4:327–331 (1985); Chollet et al., *Nucleic Acids Res.* 13:1529–1541 (1985)), fluorescent dyes (Cardullo et al., supra; Murchie et al., *Nature* 341:763–766 (1989); Clegg et al., supra; Cooper and Hagerman, supra), EDTA (Dreyer and Dervan, *Proc. Natl. Acad. Sci. USA* 82:968–972 (1985)), or alkaline phosphatase (Jablonski et al., *Nucleic Acids Res.* 14:6115–6128 (1986)) to form oligonucleotide conjugates. Applications of these modified oligonucleotides include: (i) nonradiolabeled hybridization probes (Chu and Orgel, supra; Chollet et al., supra; Jablonski et al., supra; Connolly, B. A., *Nucleic Acids Res.* 15:3131–3137 (1987)); (ii) sequence-specific cleavage of DNA (Dreyer and Dervan, supra); (iii) automated DNA sequencing (Brumbaugh et al., *Proc. Natl. Acad. Sci. USA* 85:5610 (1988)); and (iv) affinity chromatography (Ruth et al., *Fed. Proc.* 44:1622 (1985)). Moreover, this approach allows application of fluorescence spectroscopic techniques to structural studies of nucleic acids (Murchie et al., supra; Clegg et al., supra; Cooper and Hagerman, supra).

In the method of the present invention, the modified oligonucleotides containing primary amines are derivatized with fluorescent probes, as discussed above, and are used in a continuous assay to detect nucleic acid cleavage in vitro, by monitoring increases in fluorescence.

The second embodiment of this invention is directed to the application of this fluorescent assay to other less efficient enzymes involved in nucleic acid cleavage, such as retroviral integrase proteins (IN).

Integration of viral DNA into the host chromosome is an essential step in the life cycle of retroviruses. The integration reaction is known to be catalyzed by the integrase protein, which is encoded by the retroviral pol gene. Integration requires a particular sequence at the ends of the linear double-stranded viral DNA that is synthesized by reverse transcription from the viral RNA genome in the infected cells (Donehower et al., *Proc. Natl. Acad. Sci. USA* 81:6461–6465 (1984); Scgwartzberg et al., *Cell* 37:1043–1052 (1984); Panganiban et al., *Proc. Natl. Acad. Sci. USA* 81:7885–7889 (1984); Hippermeyer et al., *Virology* 137:358–370 (1984); Clavel et al., *J. Virol.* 63:1455–1459 (1989); Grandgenett et al., *Cell* 60:3–4 (1990); Varmus et al., "Retrovirus," in *Mobile DNA*, Berg, D. E. and Howe, M. M., eds., American Society for Microbiology, Washington, D.C. (1989), pp. 53–108).

Initially, human immunodeficiency virus type 1 (HIV-1) integrase recognizes the specific DNA sequence, -CAGT at the 3' end of the viral DNA and removes two bases (GT-3') from each 3' end. Subsequently, the 3' ends expose the $CA_{OH}$ and become joined to the 5' ends of target chromosomal DNA strands at the site of integration (Fujiwara et al., *Cell* 54:497–504 (1988); Brown et al., *Proc. Natl. Acad. Sci. USA* 86:2525–2529 (1989); Fujiwara et al., *Proc. Natl. Acad. Sci. USA* 86:3065–3069 (1989)). The cleavage and joining processes seem to be a coupled event. Evidence of this is that there is no requirement of an exogenous energy source (Craigie et al., *Cell* 62:829–837 (1990); Katz et al., *Proc. Natl. Acad. Sci. USA* 89:6741–6745 (1992)). As a result of the IN mediated cleavage-ligation reaction, a gapped recombination intermediate is produced. The completion of integration must require a gap repair process, which is presumably mediated by host enzymes.

In vitro studies with short synthetic oligonucleotides corresponding to either U5 or U3 ends of viral DNA have demonstrated that the integration reaction (3'-processing and strand transfer) can be catalyzed by the purified integrase alone (Craigie et al., *Cell* 62:829–837 (1990); Katz et al., *Proc. Natl. Acad. Sci. USA* 89:6741–6745 (1992); Sherman et al., *Proc. Natl. Acad. Sci. USA* 87:5119–5123 (1990); Katzman et al., *J. Virol.* 63:5319–5327 (1989); Bushman et al., *Proc. Natl. Acad. Sci. USA* 88:1339–1343 (1991)). The only requirements for this in vitro reaction are a linear DNA substrate, integrase, and a divalent metal cation (either $Mg^{2+}$ or $Mn^{2+}$). Recent mechanistic studies of the 3' processing and strand transfer reaction indicate that the strand transfer process is a one-step reaction. In one concerted reaction, a phosphodiester bond in the target DNA is cleaved and a new bond (between viral DNA and target DNA) is formed (Engelman et al., *Cell* 67:1211–1221 (1991)). This conclusion was made by examining the stereochemical course of the reactions catalyzed by HIV-IN. The chirality of the phosphothioate in the reaction products was determined by incorporating phosphothioate of known chirality in substrate DNAs. Further in vitro studies with an oligonucleotide substrate that mimics the recombination intermediate have shown that integrase can also promote a reverse reaction termed disintegration (Chow et al., Science 255:723–726 (1992). The activities of integrase are therefore characterized as donor cutting, strand transfer, disintegration, and integration site selection.

In this second embodiment of the present invention, a continuous spectroscopic assay system was developed to characterize retroviral integrase mediated nucleic acid cleavage reactions. In this embodiment, the assay preferably employs FRET, and, consequently, a pair of fluorescent labels (fluorescent donor and acceptor). This assay was developed to combine the additive effects of the quenching of donor fluorescence due to probe-strand interactions and the quenching of donor fluorescence due to energy transfer. Such an assay would therefore display a larger recovery of the donor fluorescence.

In a preferred embodiment, a double-stranded oligonucleotide representing the U5 or U3 end of HIV-DNA, is site-specifically labeled with a pair of extrinsic fluorophores, fluorescein isothiocyanate (FITC), and eosin isothiocyanate (EITC) at the 3' end and the 5' end of the substrate DNA, respectively. A variety of fluorophores can be covalently attached to the oligonucleotide substrate, which has been modified with nucleotide analogs containing primary amines. Generally, the donor and acceptor fluorescent moieties should be selected so that the emission spectra of the donor moiety overlaps the excitation spectrum of the acceptor moiety to produce efficient non-radiative energy transfer therebetween. Such exemplary fluorophore pairs include fluorescein (fluorescence donor) and eosin (fluorescence acceptor), and fluorescein (fluorescence donor) and tetramethylrhodamine isothiocyanate (fluorescence acceptor). Other suitable donor-acceptor combinations that can be utilized in the method of the present invention will be known to the skilled artisan. Further guidance on appropriate fluorescent label combinations can be found in U.S. Pat. No. 4,996,143, columns 5–6.

The two different fluorophores (fluorescent donor and fluorescent acceptor) can easily be manipulated to be in close proximity. This can be accomplished either by introducing them to the same strand of DNA or by modifying two separate strands followed by annealing. The donor fluorescence will be quenched as energy is transferred to the acceptor. Upon physical separation of these two fluorophores by enzymatic cleavage, the quenched donor fluorescence will be recovered as FRET is lost. Since HIV integrase will recognize the 3'-TGAC and cleave the 3'-TG exposing the $CA_{OH}$-3' while the 5'-end complementary sequence, ACTG, will not be cleaved by HIV-IN, the fluorescein group attached to the 3'-end would be removed from the DNA substrate, resulting in a loss of energy transfer between fluorescein and eosin. Therefore, enzymatic cleavage of the substrate will result in enhancement of the quenched fluorescence signal. Hence, monitoring these fluorescence changes detects DNA cleavage reactions of HIV-IN.

One advantage of utilizing the enhancement of fluorescence is that it will serve to amplify the observed cleavage signal. For example, if the fully recovered donor fluorescence is 10 fold higher than the quenched fluorescence, 10% DNA cleavage will still exhibit a two-fold increase in the donor fluorescence. Since HIV-IN usually displays incomplete cleavage activity, the amplification of the signal is an important feature of this fluorescence system. FRET further allows one to measure the separate processes that are involved in DNA integration and repair systems. Fluorescence offers numerous measurable parameters that with various systems can be adapted to detect fluorescent bands upon gel electrophoresis capable of detecting as little as 4 picograms of double-stranded DNA (Glazer et al., Proc. Natl. Acad. Sci. USA 87:3851 (1990)) or to monitor numerous samples in a 96-well fluorescence microplate reader. More importantly, a fluorescence assay is continuous, making it possible to obtain precise kinetic parameters for mechanistic studies of integrase proteins. A further advantage is that the degree of donor fluorescence quenching is easily manipulated in a range of 10 to 40-fold, depending on the pair and distance between the pair of fluorophores. (Matayoshi et al., Science 247:954–957 (1990)). This assay system would also provide rapid and sensitive measurements on the effectiveness of specific inhibitors on HIV-IN or other well-studied retroviral integrase proteins, such as the integrase protein of Moloney Murine Leukemia Virus (MoMLV) (Craigie et al., Cell 62:829–837 (1990)) and avian sarcoma-leukosis virus (ASLV) (Terry et al., J. Virol. 62:2358–2365 (1988)).

The described fluorometric assay for detecting nucleic acid cleavage can also be utilized to improve the efficiency and detection signal of a number of well-known procedures for amplifying or detecting a specific DNA or RNA sequence, such as polymerase chain reaction (PCR), ligase chain reaction, and catalytic hybridization amplification or "cycling probe" technology.

Having now generally described this invention, the same will be better understood by reference to one or more specific examples. These examples are included herein for purposes of illustration only and are not intended to be limiting unless otherwise specified.

EXAMPLE 1

Fluorometric Assay for Detecting Nucleic Acid Cleavage by the Restriction Enzyme, BamHI Materials FITC and 5-carboxyfluorescein were obtained from Molecular Probes (Eugene, Oreg.). The BamHI restriction enzyme was purchased from New England Biolab. Aminolink 2 and reagents for oligonucleotide synthesis were obtained from Applied Biosystems. DNase I was obtained from Worthington Enzymes.

Methods

Preparation of fluorescent-labeled oligonucleotides: Aminolink 2 is a commercially available modified base that can be directly introduced into oligonucleotides with a DNA synthesizer. This reagent introduces an aliphatic primary amine at the 5' ends of oligonucleotides. Accordingly, a 14-mer aminolink oligonucleotide, 5'-NH$_2$-CCCCGGATCCACCC-3' (SEQ ID NO:1), containing the BamHI restriction site GGATC, and its complementary strand without aminolink, 3'-GGGGCCTAGGTGGG-5' (SEQ ID NO:2), were synthesized using an Applied Biosystems 380B DNA synthesizer. The oligonucleotides were purified by an HPLC Zorbak bio series oligo column (DuPont). The aminolink oligonucleotide was then derivatized with FITC in 100 mM NaHCO$_3$/Na$_2$CO$_3$ buffer, pH 9.0. The FITC was initially dissolved in DMF and then added to the oligonucleotide solution (20% v/v). Excess dye was removed by filtration of the reaction mixture through a Sephadex G-25 column (DNA grade). The resulting sample and its complementary strand were then electrophoresed on denaturing (7M urea) 20% polyacrylamide gels to further purify the oligonucleotides and to remove any residual free dyes. The appropriate oligonucleotide bands were sliced from the gels and electroeluted using the S&S ELUTRAP Electro-Separation System (Schleicher & Schuell).

Spectroscopic Measurements: Absorbance and absorption spectra were measured with a Hewlett-Packard 8450A diode array spectrophotometer. Using the extinction coefficient of fluorescein (E-78,000) at 492 nm, the concentration and total moles of fluorescein were calculated (Chen and Scott, supra). The amount of fluorescein conjugated to the oligonucleotide was estimated by subtracting the moles of fluorescein multiplied by the extinction coefficient of FITC at 260 nm, 23,000$M^{-1}$ $cm^{-1}$, from the total absorbance at 260 nm. The remaining $AU_{260}$ should be proportional to the DNA content. Steady-state fluorescence spectra and intensity were recorded with an SLM 8000 spectrophotofluorometer with 10-mm Glan-Thompson polarizers. Fluorescence emission measurements were performed under "magic angle" emission conditions (Spencer and Weber, J. Chem. Phys. 52:1654–1663 (1970)). A cuvette with a 3-mm excitation path length was used for all experiments. The absorbance of all fluorescence samples was less than 0.1 at the wavelength of excitation to avoid inner-filter effects. The temperatures of the samples were regulated with a Neslab Instruments, Inc., T.E.Q. temperature controller and a PBC4 bath cooler.

Time-resolved fluorescence was measured on a time correlated single-photon counting instrument. Excitation was accomplished by a synchronously pumped, mode-locked, cavity dumped dye laser (Spectra-Physics 2045E argon/ 3520 dye) capable of producing 10-ps (fwhm) pulses at a frequency of 4 MHz, which are frequency doubled to UV. Time-resolved experiments were also performed under "magic angle" conditions. The excitation wavelength was 310 nm, and the emission wavelengths were selected via a stepper motor-driven monochromator. 1,8-ANS and 5-carboxyfluorescein were used as fluorescence standards to verify proper functioning of the instrument, and to correct for the wavelength-dependent transmit time of the Hamamatsu R955 photomultiplier. All fluorescence measurements were performed with the samples in 50 mM Tris-HCl, pH 8.0, 10 mM $MgCl_2$, and 0.1M NaCl, which is the optimal buffer condition for BamHI cleavage reactions.

The extent of cleavage by BamHI was calculated from the fluorescence data utilizing the following equation:

$$[DNA]_c = \frac{F_t - F_0}{F_\infty - F_0} \times [DNA]_i \quad \text{(Equation 1)}$$

where $[DNA]_c$ is the concentration of cleaved DNA, $F_t$ is the fluorescence intensity at time, t, $F_\infty$ is the fluorescence intensity at the plateau, $F_0$ is the initial fluorescence intensity, and $[DNA]_i$ is the initial concentration of DNA.

Results and Discussion

The quenching of fluorophores attached to oligonucleotides via Aminolink 2 (six carbon chain linker) has been previously described (Murchie et al., supra; Clegg et al., supra; Cooper and Hagerman, supra). This quenching was attributed to direct interactions between the probes and the DNA. To further characterize this quenching behavior, a 14-mer BamHI target oligonucleotide was synthesized that includes a primary amino group introduced at the 5'-end via Aminolink 2. The resulting amino group was then derivatized with FITC in 100 mM $NaHCO_3/Na_2CO_3$, pH 9.0, and 20% DMF.

Both steady-state and time-resolved fluorescence measurements were employed. Initially, the steady-state fluorescence intensity of the FITC-labeled single-strand and the double-strand annealed to its nonlabeled complementary strand were compared. To a fixed concentration of FITC-labeled oligonucleotides (0.137 pmol), varying concentrations of the unlabeled complementary strands were added and annealed in 0.5 mL of 50 mM Tris-HCl, pH 8.0, 10 mM $MgCl_2$, and 0.1M NaCl. Changes in the emission spectra of fluorescein were monitored with an excitation wavelength of 490 nm at 37° C. FIG. 1 shows the progressive quenching of fluorescence due to the increasing degrees of annealing. Approximately two fold quenching of fluorescein intensity was observed when the labeled oligonucleotide was annealed to equal concentrations of nonlabeled sample. Further quenching of fluorescence was not observed when a 1.5M excess concentration of unlabeled complementary strand was added, indicating that changes in fluorescein intensity were primarily due to the degree of annealing. The annealed complex also displayed blue-shifted emission spectra. To confirm that the observed quenching is associated with annealing and to examine if this process is reversible, an excess concentration of DNase I was added. As shown in FIG. 1, the initial fluorescence intensity was fully recovered (compared to that of the single-strand).

Figure 2B:
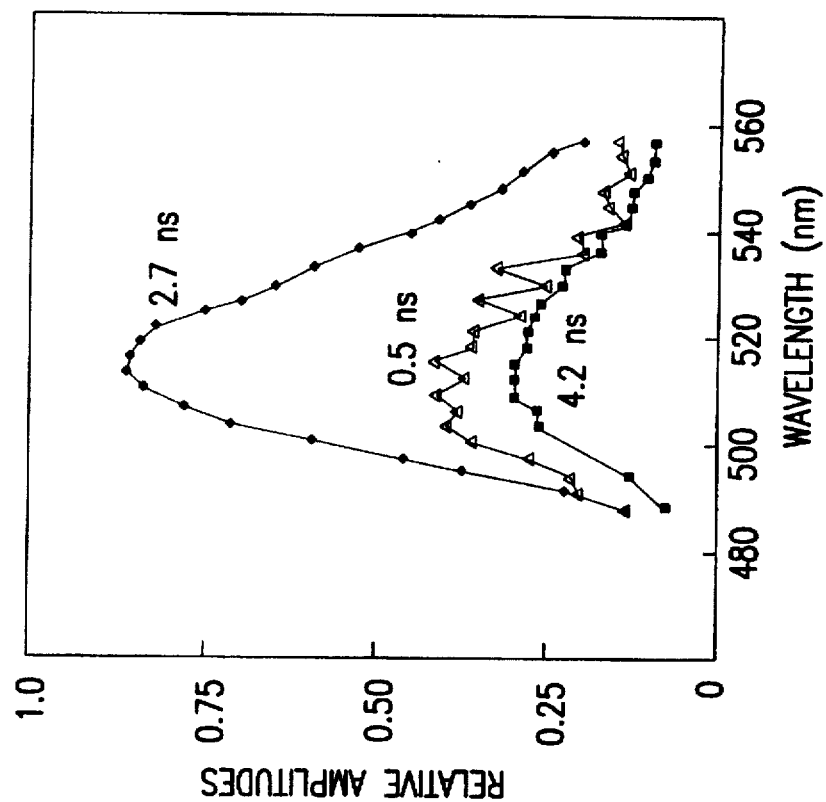
FIGS. 2A and 2B.
Figure 2A:
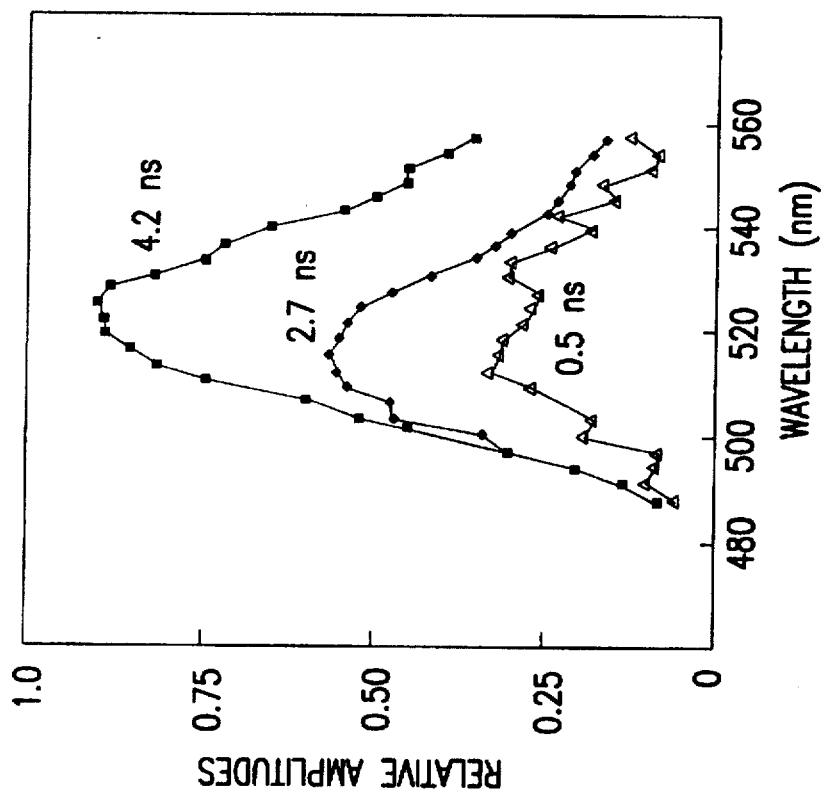

The aforementioned quenching was characterized with time-resolved fluorescence studies. A series of decay curves was collected as a function of emission wavelength from both the single-strand and annealed samples. The decay curves were simultaneously analyzed using a global analysis procedure (Knutson et al., Chem. Phys. Lett. 102:501–504 (1983); Beechem et al., Anal. Instrum. 14:379–402 (1985)). The best fit of the data was achieved by triexponential decay analysis. The recovered decay components were 0.5, 2.7, and 4.2 ns (FIGS. 2A and 2B). The single-strand sample exhibits a predominant decay component of 4.2 ns (FIG. 2A). Upon annealing, this component was severely decreased (FIG. 2B). The decay-associated spectra of the two minor decay components were blue-shifted compared to the decay-associated spectrum of the 4.2 ns component. Hence, pure static quenching (and/or loss of the corresponding absorbing species in the ground state) of the 4.2 ns component results both in loss of steady-state intensity and in the emergent blue-shift of the steady-state spectra. These results confirm previous observations regarding labeled oligonucleotides (Clegg et al., supra; Cooper and Hagerman, supra).

Since DNase I reversed the quenching of the double-strand DNA fragment at 37° C., the DNA cleavage process of the restriction endonuclease BamHI was examined by monitoring changes in the fluorescence intensity. The Type II restriction endonuclease BamHI recognizes the duplex symmetrical sequence 5'-GGATCC-3' (Wilson and Young, J. Mol. Biol. 97:123–125 (1975)). Accordingly, oligonucleotide samples containing this recognition sequence were synthesized as shown below:

5'-FITC- NH- CCCCGGATCCACCC-3'  (SEQ ID NO:1)
3'-GGGGCCTAGGTGGG-5'  (SEQ ID NO:2)

To ensure complete annealing of the ends of the oligonucleotides, consecutive cytosines and guanines were designed at both ends. In the presence of $Mg^{2+}$, the enzyme catalyzes double-strand cleavage between the guanines, generating 5'-phosphoryl and 3'-hydroxyl staggered termini. Cleavage by the BamHI restriction endonuclease results in the fragments:

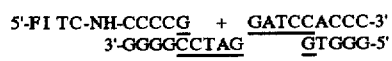

5'-FITC-NH-CCCCG  +  GATCCACCC-3'
3'-GGGGCCTAG       GTGGG-5'

The cleaved products will be two fragments of 5 base pairs each; these should have relatively low melting temperatures.

Figure 3B:
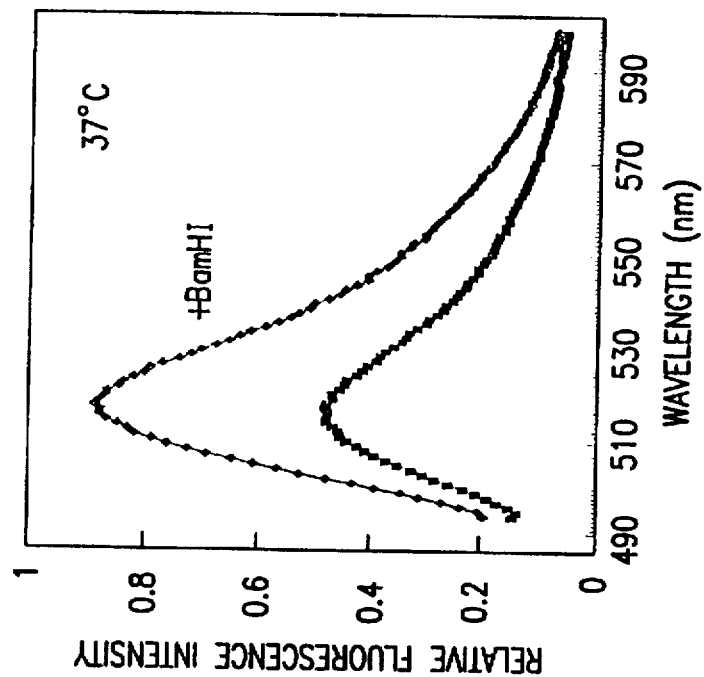
FIGS. 3A and 3B.
Figure 3A:
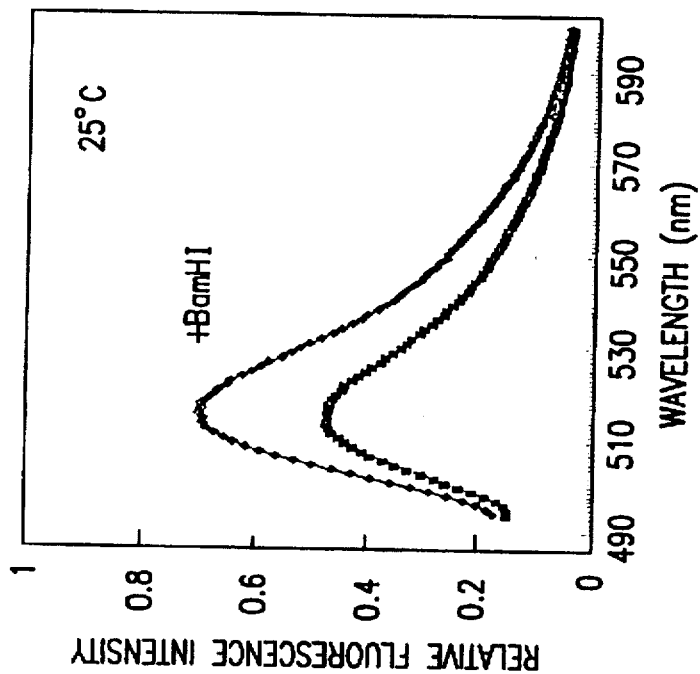

Dissociation of the two strands should result in total recovery of fluorescence intensity. FIGS. 3A and 3B depict the changes in fluorescence intensity due to the BamHI restriction endonuclease. The labeled oligonucleotide (0.208 nmol) was annealed with a 1.5M excess concentration of unlabeled complementary strand and then digested with 20 units of BamHI in a 400 µl solution containing 50 mM Tris-HCl, pH 8.0, 10 mM $MgCl_2$, and 0.1M NaCl. The cleavage experiments were monitored at both 25° C. (FIG. 3A) and the optimal temperature for BamHI cleavage, 37° C., (FIG. 3B) to determine any differences in the extent of fluorescence recovery. The emission spectra of the cleaved samples were recorded with an excitation wavelength of 490 nm after the fluorescence changes at an emission wavelength of 520 nm had reached a plateau. As expected, both samples resulted in increased fluorescence intensity compared to the uncleaved DNA at both temperatures. To compare the differences observed in the extent of fluorescence recovery, the intensities of the samples at both temperatures were peak normalized according to the values of uncleaved substrates. It was also observed that changes in fluorescence intensity occurred only with annealed samples in the presence of $Mg^{2+}$. No changes in fluorescence were observed with the single-strand alone, annealed samples in the presence of EDTA, or after the methylation of the substrate by BamHI methyltransferase, indicating that the observed fluorescence changes are the direct result of cleavage by BamHI.

It was noted that the changes in fluorescence intensity were significantly greater at 37° C. than at 25° C. This discrepancy could be accounted for by the incomplete dissociation of the 5-mer products to their single-strand components at 25° C. Using the computer program OLIGO (Rychlik and Rhoads, *Nucleic Acids Res.* 17:8543–8551 (1989)), the predicted $T_m$ of the 5-mer sequence by percentage GC methods is $-12.5°$ C., whereas the predicted $T_m$ using (AT * 2° C.+GC * 4° C.) (Suggs et al., in *ICN-UCLA Symposium on Development of Biology Using Purified Genes*, Brown (ed.), Academic Press, Inc., New York (1981), pp. 683–693) is 20° C. These formulae give an estimated temperature at which 50% of the oligonucleotide duplexes are dissociated. Therefore, it would be expected from the latter formula that all of the 5-mer sequences would not dissociate to their respective single-strands at room temperature (25 ° C.), whereas all of the cleaved products would dissociate at 37° C.

Figure 4:
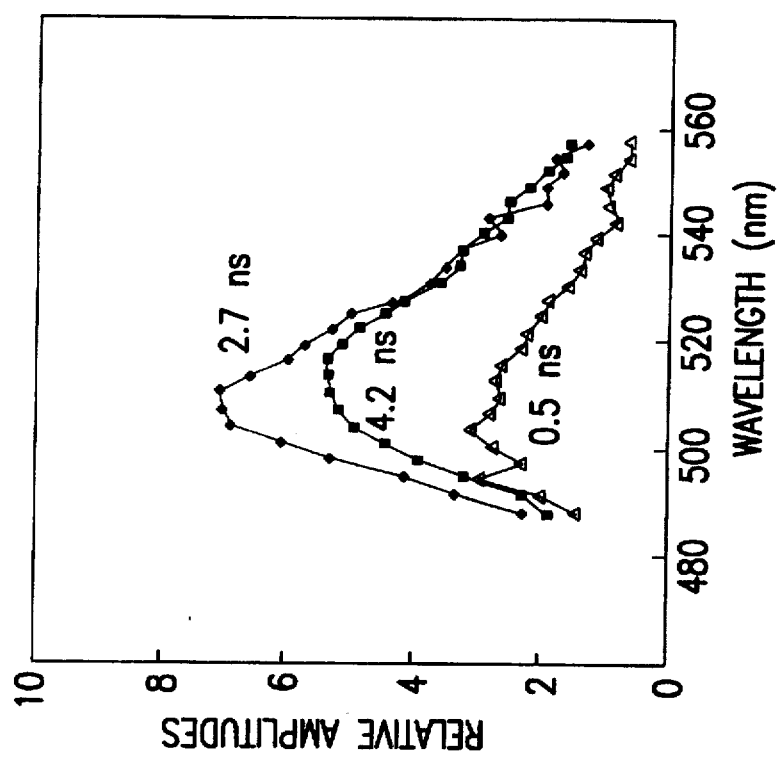
FIG. 4 is a graph depicting the decay-associated spectra of FITC-labeled DNA substrate after the cleavage reaction by the BamHI restriction endonuclease. The experiment was performed in 50 mM Tris, pH 8.0, 10 mM $MgCl_2$, and 0.1M NaCl at 25° C.

Time-resolved studies were also performed with the cleaved products of the FITC-labeled DNA substrates at 25° C. Once again, a series of decay curves was collected as a function of emission wavelength (FIG. 4). The cleaved sample exhibits the same three decay components found for annealed and single-stranded samples. As expected, the amplitude associated with the 4.2 ns component had increased compared to that of the uncleaved (annealed) sample. However, the 4.2 ns component did not fully recover to the original amplitude of the single-strand sample. Since these decay measurements were performed at 25° C., the prior (incomplete dissociation) effects observed in FIG. 3A could account for the lack of complete recovery.

Both the results above and the DNase I data (FIG. 1) demonstrate that full recovery of fluorescence intensity is observed at 37° C. However, examining the possibility of partial dissociation of the double-stranded DNA substrate was also deemed important. As expected, the single-stranded sample showed a decrease in intensity as temperature increased due to an increased rate of internal conversion, which decreases the observed fluorescence. In contrast, the fluorescence intensity of the annealed sample increased with temperature.

Figure 5:
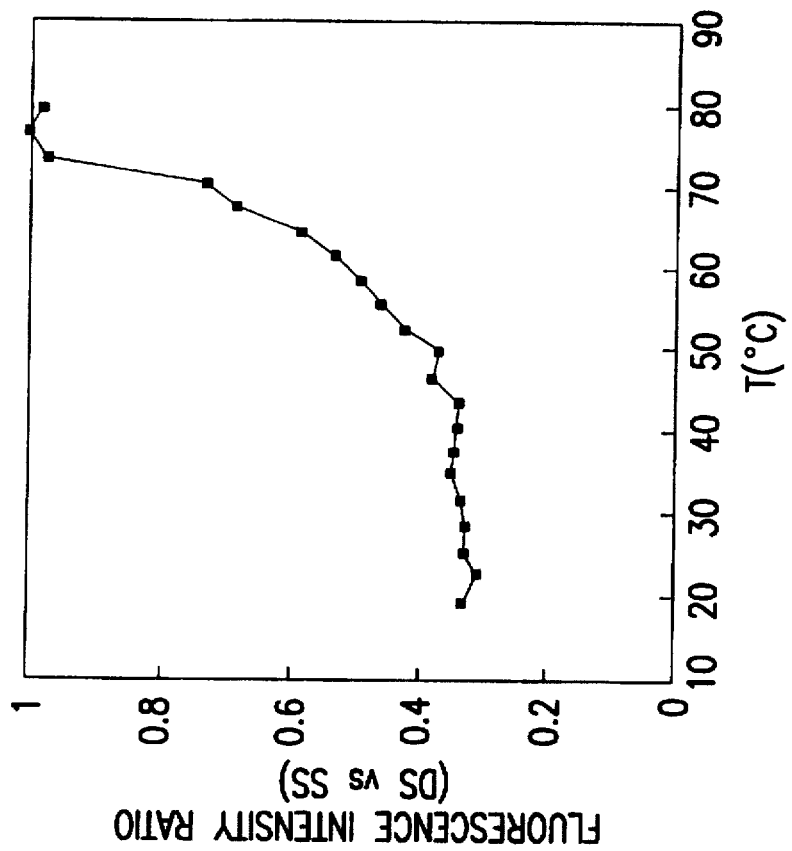
FIG. 5 is a graph depicting the temperature-dependent fluorescence intensity ratio of double-strand and single-strand FITC-labeled oligonucleotides. The thermally induced fluorescence changes were monitored at 520 nm with an excitation wavelength at 490 nm.

To correct for the direct temperature effects on fluorescence intensity, the intensity ratio of the double-stranded and single-stranded samples was plotted as a function of temperature (FIG. 5). Subsequently, the apparent melting temperature of the annealed double-stranded sample was obtained. The predicted $T_m$ of the annealed sample using AT * 2° C.+GC * 4° C. is 50° C., whereas the predicted $T_m$ using percentage GC methods is 65.5° C. These results suggest a $T_m$ for the double-stranded sample of approximately 65° C., which is in better agreement with the percentage GC method. It should be emphasized that there are no significant changes in fluorescence intensity observed in the temperature range from 20° C. to 45° C., ensuring that the optimal assay conditions for BamHI are in the thermally stable region for the annealed substrate.

Figure 6B:
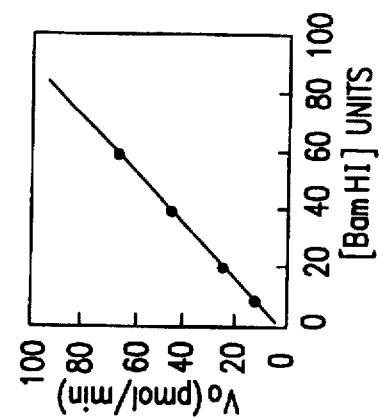
FIGS. 6A and 6B.
Figure 6A:
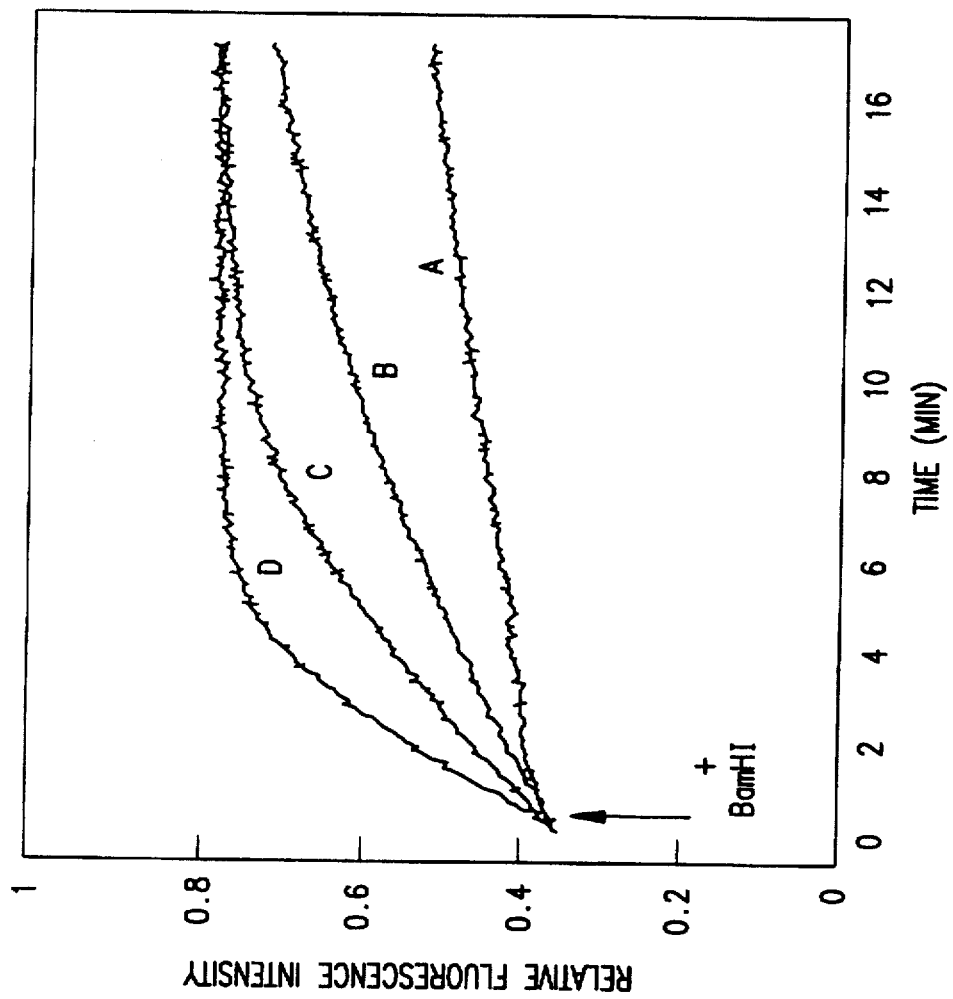

Utilizing this information, the kinetics of DNA cleavage by BamHI was subsequently studied at 37° C. Differing concentrations of the enzyme (10, 20, 40, and 60 units) were added to a fixed concentration of substrate, 0.208 nmol, in 420 µl of 50 mM Tris-HCl, pH 8.0, 10 mM $MgCl_2$, and 0.1M NaCl. FIG. 6 shows how the apparent rates of cleavage increase as a function of enzyme concentration. These rates are the composite of two processes: cleavage of the substrate by BamHI and the subsequent dissociation of the cleaved products into their single-strand components. The rate-limiting step of the overall process is cleavage by BamHI. For reasons discussed previously, the rate of dissociation will not contribute to the observed rates of cleavage because dissociation of the 5-mer sequences should be relatively fast at 37° C. Initial velocities were determined from the linear portions of the curves (FIG. 6, inset). The plot of the initial velocities versus enzyme concentrations was linear, suggesting that the rate of cleavage was first order with respect to BamHI concentration, and that the rates observed were due to cleavage of the substrate.

Figure 7A:
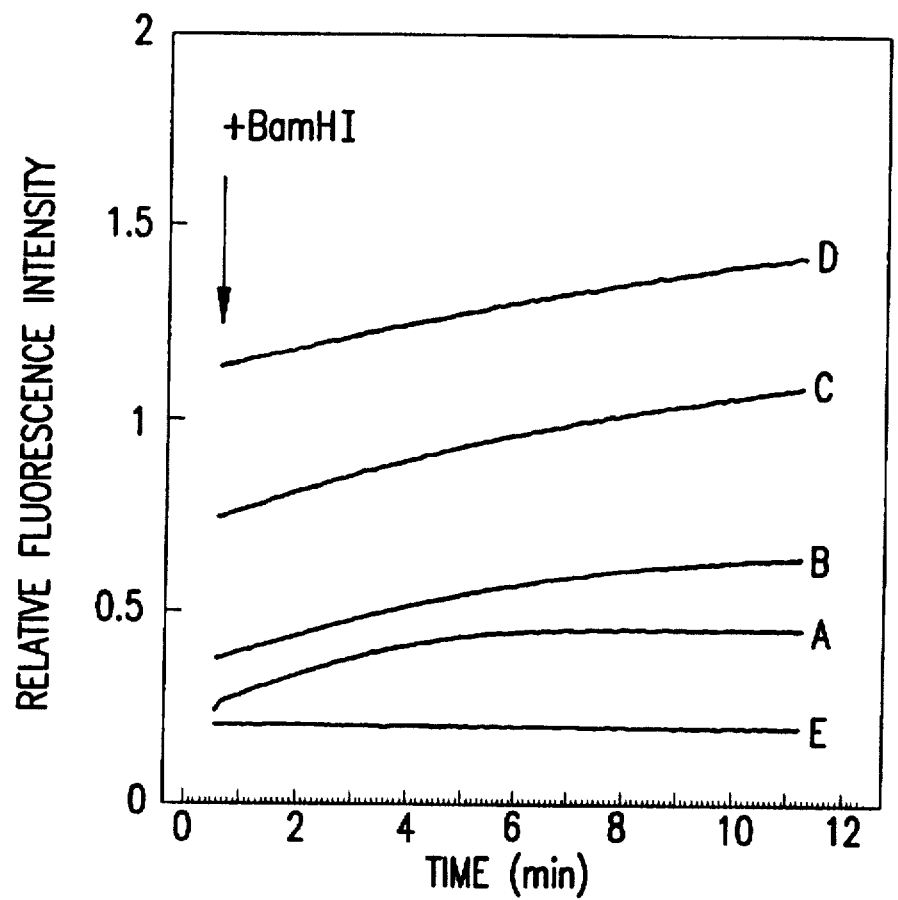
FIGS. 7A and 7B.
Figure 7B:
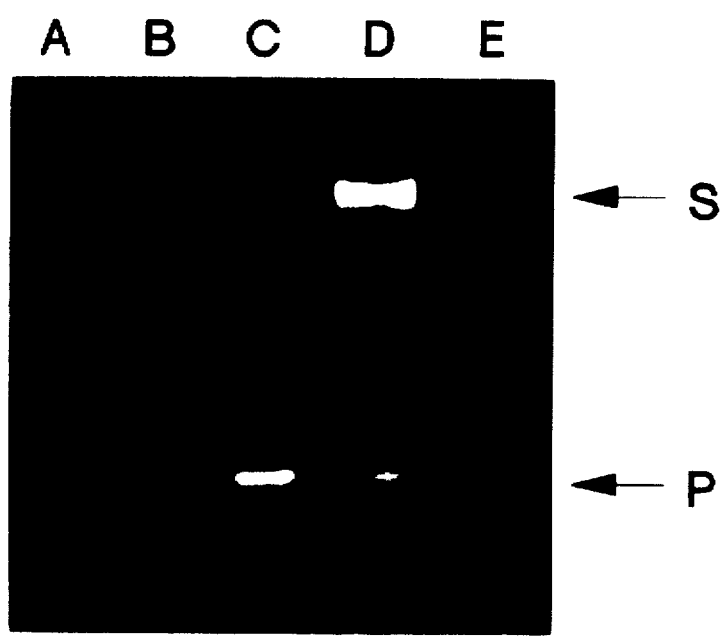

Cleavage reactions were also examined as a function of substrate concentration with a fixed concentration of BamHI (10 units in 100 µl total reaction volume). The reactions were initiated by the addition of BamHI and stopped by the addition of 25 mM EDTA 11 minutes after the enzyme was added. The reaction mixtures were subjected to native 20% polyacrylamide gel analysis. Since the DNA substrate was labeled with FITC, a photograph of the gel was taken under ultraviolet illumination (using a Kodak green filter) without staining the gel with ethidium bromide. Therefore, only the fluorescent-labeled DNA fragments were visualized, resulting in two DNA bands: a substrate band and a product band (5'-FITC-NH-CCCCG). A direct comparison was made between the data obtained from the fluorometric assay and the photographic data obtained from gel electrophoretic analysis. The kinetics of BamHI cleavage reactions as a function of DNA substrate concentration measured by fluorometric analysis are illustrated in FIG. 7A. In the presence of 25 mM EDTA, no changes in fluorescence intensity were observed (curve E), indicating that no cleavage of the substrate occurred. The fluorescence intensity at low concentrations of substrate (0.21 µM, curve A) was observed to plateau approximately 6 minutes after the initiation of reaction. This indicates that the reaction reached completion; i.e., there was no more substrate available for cleavage. This conclusion was further confirmed by data obtained from gel electrophoresis analysis, which showed 100% conversion of substrate to the product (FIG. 7B, lane A). Similarly, the reaction at 0.36 µM substrate reached near completion as shown by both the fluorescence (curve B, FIG. 7A) and the gel data (lane B, FIG. 7B). Higher DNA substrate concentrations, 0.72 µM (curve C, FIG. 7A) and 1.08 µM (curve D, FIG. 7A), yielded incomplete cleavage reactions (observed by changes in fluorescence intensity). The time frame depicted here does not allow the reaction to go to completion at high substrate concentrations. Curve C, however, shows higher net fluorescence changes than those observed for curve D, indicating that more cleavage products should be observed for C. It appears that the initial velocity of curve D is also slower than that of curve C. These results may be due to pipeting error since the reaction is initiated by the addition of 0.5 µl of BamHI (20 units/µl) that is stored in 50% glycerol. As expected, the PAGE data (FIG. 7B) show higher product formation in lane C compared to that of lane D.

The results of both sets of data are summarized in Table 1. The fractions of uncleaved and cleaved DNA were calculated from the fluorescence data utilizing equation 1 (see Methods). Fractions of uncleaved and cleaved DNA were also estimated from a photograph taken from the polyacrylamide gel. Utilizing a Hewlett Packard ScanJet IIp and the densitometry program Scan Analysis 68000 (BioSoft), the peaks obtained from each of the bands (substrate and products) were integrated and ratioed to obtain the relative amount of cleavage. As illustrated in Table 1, the data obtained from the fluorescence measurements correlate well with those obtained from the gel, confirming the viability of the kinetic assay.

TABLE 1

Summary of Percentage Cleavage of FITC-labeled DNA Substrates by BamHi, Estimated by Both Fluorometric and PAGE Analysis

| Curves | [DNA] µM | % Cleavage Fluorescence Assay | % Cleavage PAGE |
|--------|----------|-------------------------------|-----------------|
| A      | 0.21     | 100                           | 100             |
| B      | 0.36     | 91.9                          | 92.3            |
| C      | 0.72     | 59.5                          | 60.6            |
| D      | 1.08     | 32.2                          | 30.1            |
| E      | 0.18     | 0                             | 0               |

In summary, using the BamHI restriction endonuclease as an exemplary system, the results presented in this Example demonstrate the feasibility of applying the fluorescence "dequenching" phenomenon to kinetic studies of other restriction endonucleases. The fluorescence assay presented herein provides an easy and rapid method for acquiring high data density essential for precise kinetic studies (e.g., quantifying sequence discrimination by base-analog substitutions). It should also be possible to employ this approach to develop a coupled assay for sequence-specific DNA methylase activity. A continuous fluorometric assay is highly advantageous over the conventional discontinuous gel electrophoresis assay systems. Kinetic data obtained from this continuous system based on fluorescence dequenching may significantly improve studies of enzymatic reactions in molecular biology, and is a viable alternative to FRET in studying cleavage and strand separation processes in molecular biology.

EXAMPLE 2

Fluorometric Assay for Detecting Nucleic Acid Cleavage Mediated by HIV-integrase Materials 5-Amino (12)-2'-deoxyuridine β-cyanoethyl phosphoramidite was obtained from Molecular Biosystems, Inc. FITC, EITC, 5-carboxyfluorescein, and 1,8-ANS were purchased from Molecular Probes. [γ-$^{32}$P]ATP was obtained from ICN. T4 polynucleotide kinase was obtained from New England Biolabs. $Ni^{2+}$-charged metal chelating resin was purchased from Novagen.

Methods

Preparation of HIV-IN protein: The wild-type HIV-integrase protein was obtained from Dr. Robert Craigie (Laboratory of Molecular Biology, National Institute of Diabetes and Digestive and Kidney Diseases, Bethesda, Md.). The protein was overexpressed in *Escherichia coli* and purified according to previously-described procedures. (Sherman and Fyfe, *Proc. Natl. Acad. Sci. USA* 87:5119–5123 (1990)).

Preparation of Oligonucleotides and Fluorescent Labeled DNA Substrate for HIV-IN: Oligonucleotides containing the terminal sequence of HIV-1 DNA were synthesized using a DNA synthesizer and annealed to form the following substrates:

Substrate 1:
F-D1/T1: TGAGTACCCGTGTGGAAAATCTCTAGCAGGGNCTATGGCGTCCCCTCTG (SEQ ID NO:3)
E-D2: ACTCATGGGCACACCTTTTAGAGATCGTCAN (SEQ ID NO:4)

Subtrate 2:
F-D1/T1: TGAGTACCCGTGTGGAAAATCTCTAGCAGGGNCTATGGCGTCCCCTCTG (SEQ ID NO:3)
D3: ACTCATGGGCACACCTTTTAGAGATCGTCCCAGATACCGCAGGGGAGAC (SEQ ID NO:5)

Bold letters are the sequences of the U5 end of the HIV-1 DNA (See Smith et al., *J. Virol* 64:6286–6290 (1990)) and N depicts the position of the nucleotide analog that contains an aliphatic primary amine. F indicates FITC, E indicates EITC, D indicates donor strand, and T indicates target strand. D3 does not have a fluorescent label. The oligonucleotides were purified by an HPLC Zorbak bio series oligo column (Du Pont).

5-Amino (12)-2'-deoxyuridine β-cyanoethyl phosphoramidite is a commercially available modified base that can be directly introduced into oligonucleotides with a DNA synthesizer. This reagent substitutes for dTTP and introduces an aliphatic primary amine at the specified positions in the oligonucleotides. The D1/T1 and D2 oligonucleotides containing this nucleotide analog were then derivatized with a pair of fluorescent FITC and EITC dyes, in 100 mM $NaHCO_3/Na_2CO_3$ buffer pH 9.0, respectively. Excess dye was removed by filtration of the reaction mixture through a Sephadex G-25 column (DNA grade). The resulting samples were then electrophoresed on denaturing (7M urea) 20% polyacrylamide gels to purify further the oligonucleotides and to remove any residual free dyes. The appropriate oligonucleotide bands were sliced from the gels and electroeluted using the S&S ELUTRAP Electro-Separation System from Schleicher & Schuell.

Spectroscopic Measurements: Absorbance and absorption spectra were measured with a Hewlett-Packard 8450A diode array spectrophotometer. Steady-state fluorescence spectra and intensity were recorded with an SLM 8000 spectrophotofluorometer with 10-mm Glan-Thompson polarizers. Fluorescence emission measurements were performed under "magic angle" emission conditions (Spencer and Weber, *J. Chem. Phys.* 52:1654–1663 (1970)). A cuvette with a 3 mm excitation path length was used for all experiments. The absorbance of all fluorescence samples was less than 0.1 at the wavelength of excitation to avoid inner filter effects. The temperatures of the samples were regulated with a Neslab Instruments, Inc. T.E.Q. temperature controller and a PBC4 bath cooler.

Time-resolved fluorescence was measured on a time correlated single-photon counting instrument. Excitation was accomplished by a synchronously pumped, mode-locked, cavity dumped dye laser (Spectra-Physics 2045E argon/ 3520 dye) capable of producing 10 ps (fwhm) pulses at a frequency of 4 MHz, which are then frequency doubled to UV. Time-resolved experiments were also performed under "magic angle" conditions. The excitation wavelength was 310 nm, and the emission wavelengths were selected via a stepper motor-driven monochromator. 1,8-ANS and 5-carboxyfluorescein were used as fluorescence standards to verify proper functioning of the instrument and to correct for the wavelength-dependent transmit time of the Hamamatsu R955 photomultiplier.

Radioactive DNA cleavage reaction: One microgram of the appropriate oligonucleotide was $^{32}$P-labeled at the 5' termini by use of T4 polynucleotide kinase and 25 µCi of [γ-$^{32}$P]adenosine 5'-triphosphate. The labeled oligonucleotide was annealed with 3 fold molar excess of unlabeled complementary strand(s) in 10 mM Tris-HCl, pH 8.0, 1 mM EDTA, and 0.1M NaCl. All the reaction mixtures for the IN protein mediated cleavage reactions contained 25 mM HEPES, pH 7.5, 2.5 mM DTT, 60 mM NaCl, 5% glycerol (v/v), 7.5 mM $Mg^{2+}$, $^{32}$P labeled fluorescent substrates, and HIV-1 IN in a total volume of 15 µl. The reactions were initiated by addition of IN protein, and the reaction mixtures were incubated up to 90 minutes at 37° C. The reactions were stopped by the addition of an equal volume of stop solution (95% formamide, 30 mM EDTA, 0.1% xylene cyanol, 0.1% bromphenol blue) to each reaction and boiled for 5 minutes. Ten µl of each reaction mixture was electrophoresed on a 7M urea denaturing 15% polyacrylamide sequencing gel and reaction products analyzed by autoradiographic densitometry.

Results and Discussion

It has recently been demonstrated that the endonuclease activity exhibited by HIV-IN could be altered in terms of its efficiency of cleavage and metal requirement depending on the length and structure of substrates (Lee et al., *J. Biol. Chem.*, submitted 1994). The longer substrates that were utilized contained a 49-mer hybrid strand consisting of 19 base pairs corresponding to the sequence at the U5 end of the HIV-1 DNA, with 9 additional random base pairs at the 5' end of the donor strand, and 21 random nucleotides as the target sequence at the 3' end. This longer substrate displayed $Mg^{2+}$ dependent endonucleolytic cleavage. When the 9 random base pairs were substituted with the endogenous sequences corresponding to the U5 end of the HIV-1 DNA, the cleavage pattern was identical to the original 49-mer hybrid with a preference for $Mg^{2+}$. Therefore, the inventors concluded that increases in the length of both donor and target sequences in the hybrid strand result in the enhancement of activation by $Mg^{2+}$ over $Mn^{2+}$, bringing the in vivo and in vitro reaction conditions into agreement.

In this Example, the $Mg^{2+}$-dependent endonuclease activity of HIV-IN was further characterized utilizing fluorescence resonance energy transfer. The 49-mer hybrid strand and its partial complementary strand were modified to contain a fluorescence donor and acceptor. The sequence and the cleavage reaction of the fluorogenic substrate 1 are shown below:

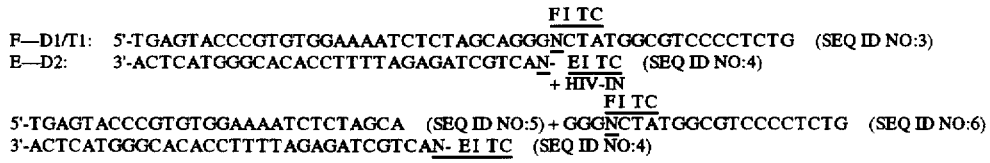

Figure 8:
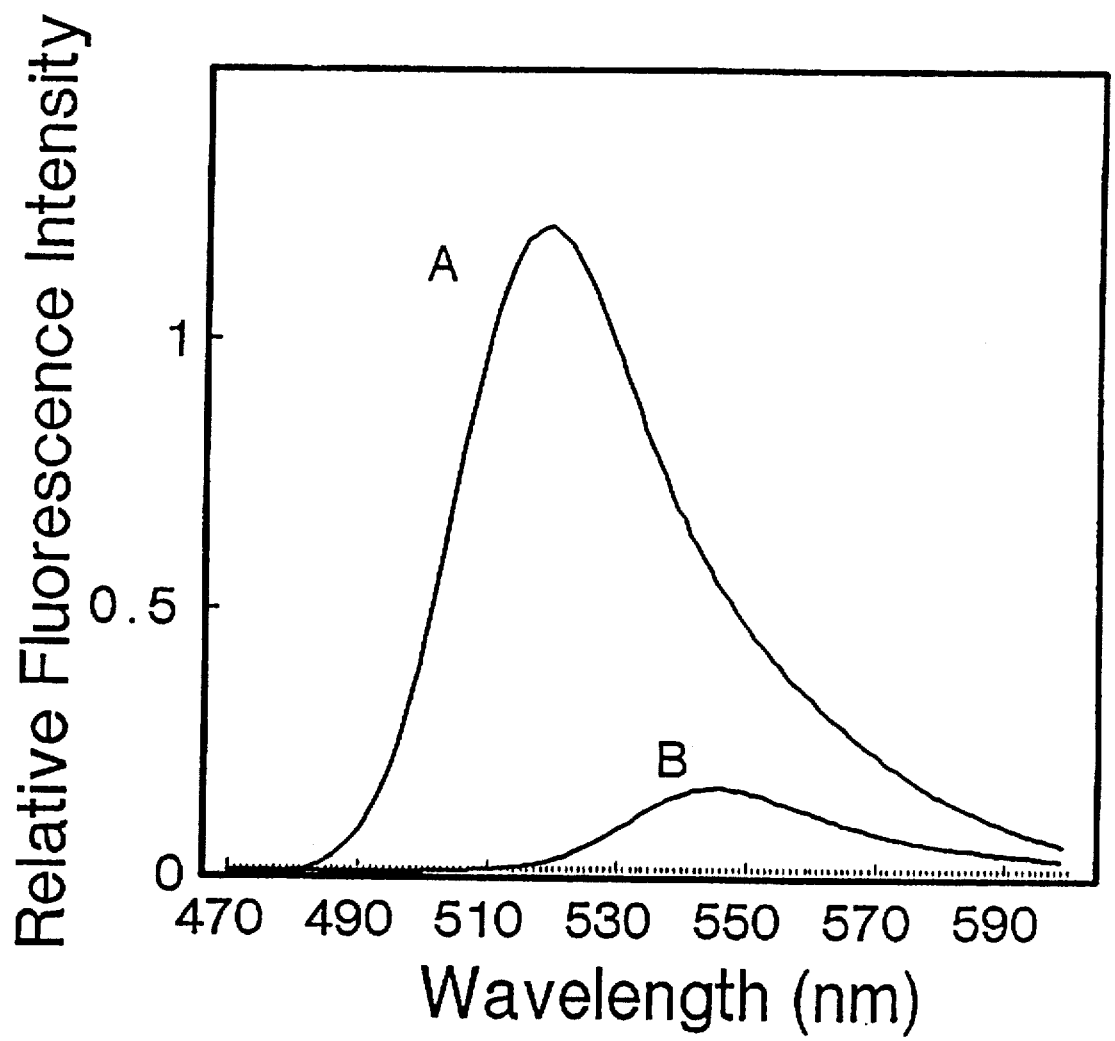
FIG. 8 is a graph depicting steady-state emission spectra of FITC and EITC labeled oligonucleotides. The spectra of F-D1/T1 (Curve A) and E-D2 (Curve B) were recorded with an excitation wavelength at 460 nm.
Figure 9A:
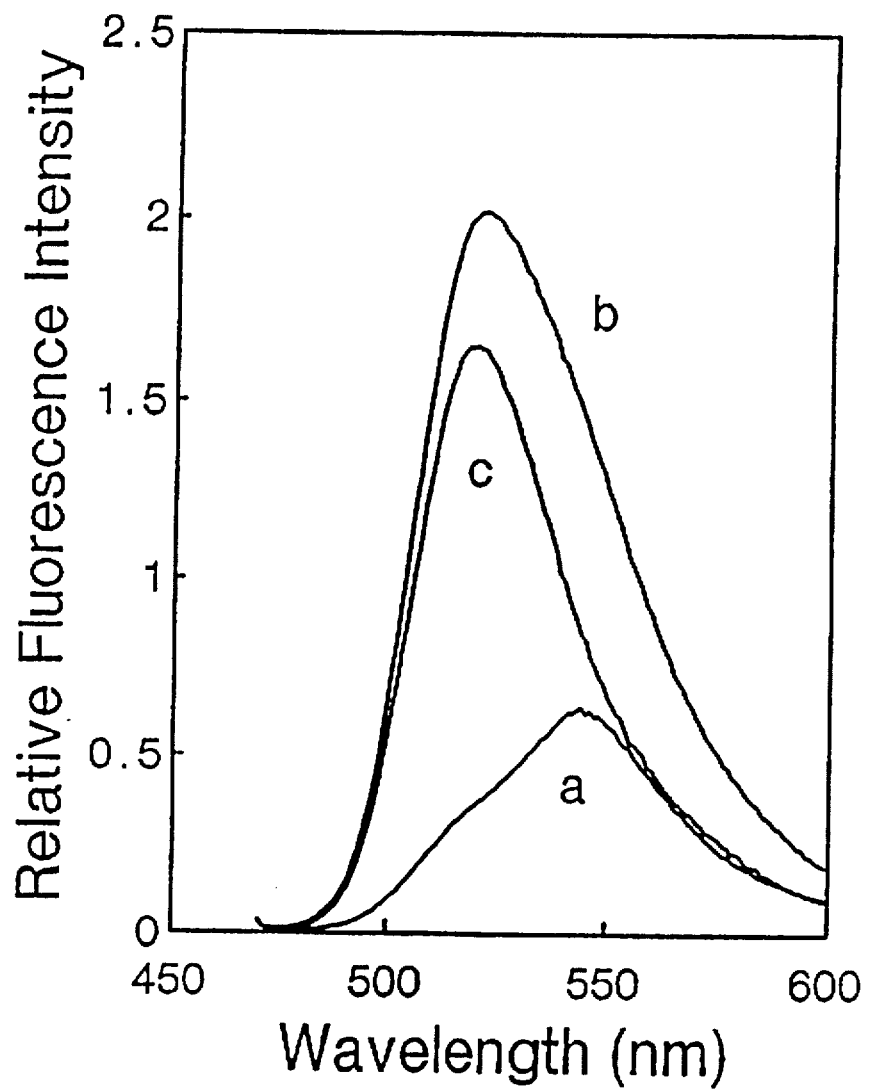

Both FITC and EITC were covalently labeled to a primary amine group of a nucleotide analog (N), 5-amino (12)-2'-deoxyuridine β-cyanoethyl phosphoramidite. This analog is introduced at specified positions in the oligonucleotides by substituting for dTTP via a DNA synthesizer. Significant resonance energy transfer from fluorescein to eosin (calculated Förster distance of 54Å, Carraway et al., *J. Biol. Chem.* 264:8699–8707 (1989)) was expected owing to the strong spectral overlap between the emission spectrum of fluorescein ($\lambda_{MAX}$=520 nm) and the absorption spectrum of eosin ($\lambda_{MAX}$=525 nm). The emission spectra of the individual oligonucleotide strands labeled with fluorescein and eosin are shown in FIG. 8. Annealing of the fluorescein labeled strand to the eosin labeled strand resulted in severe quenching of the donor fluorescence, as shown in FIGS. 9A and 9B.

As depicted in the above reaction, HIV-IN precisely cleaves the hybrid strand at the junction between CA and GG in the presence of $Mg^{2+}$, thereby producing a 28-mer donor strand and a 21-mer target strand. Cleavage of the fluorogenic substrate will result in the physical separation of the two fluorophores and subsequent recovery of the quenched donor fluorescence. It was reasoned that the distance dependent process of FRET could be utilized to monitor the DNA cleavage reaction by HIV-IN.

Initially, changes in fluorescence intensity due to cleavage of the substrate by DNase I digestion in the presence of both $Mg^{2+}$ and $Mn^{2+}$ were examined. As shown in FIGS. 9A and 9B, cleavage of the substrate by DNase I resulted in a dramatic increase in the donor fluorescence intensity. Full recovery of the donor fluorescence for both cations was observed as determined by comparison to the intensity of the fluorescein labeled single-strand. The enhancement of the donor fluorescence was further accompanied by a significant spectral shift due to the increase in the donor emission and reduction in the acceptor emission. These changes are characteristic of resonance energy transfer.

It should be noted that the intensity ratio of the donor fluorescence in the absence and presence of its energy acceptor is approximately 10 fold. Therefore, one advantage of utilizing FRET is that it provides a method for amplifying the detecting signal. Since HIV-IN usually displays incomplete cleavage activity, the amplification of the signal is an important feature of the fluorescence system. More importantly, it provides a tremendous advantage in terms of its sensitivity and specificity, since this signal amplification increases the signal-to-noise ratio of the fluorescence data.

Furthermore, the DNase I reaction performed in the presence of $Mg^{2+}$ and $Mn^{2+}$ showed that $Mn^{2+}$ results in quenching of the fluorescence. When the spectrum in FIG. 9B was peak normalized to that in FIG. 9A, no spectral changes were observed (shown in the inset). Therefore, the observed quenching in the presence of $Mn^{2+}$ was the result of a static quenching process of both the donor and acceptor fluorescence. Although $Mn^{2+}$ does not cause complications in interpreting the fluorescence data, it does reduce the sensitivity of the fluorescence detection. Therefore, $Mg^{2+}$ is the preferred divalent cation for fluorescence studies.

The emission spectra shown in FIG. 11 illustrate the fluorescence study performed with HIV-IN in the presence of 7.5 mM $Mg^{2+}$. The increase in donor fluorescence intensity represents DNA cleavage catalyzed by HIV-IN. As mentioned earlier, the shape of the emission spectrum, as a result of cleavage (spectrum B), was different than the spectrum of the substrate without the addition of the enzyme (spectrum A). It should be noted that the shape of the difference spectrum is virtually superimposable with the emission spectrum of donor FITC-labeled single-strand (F-D1/T1). There is a small reduction in the 520–600 nm wavelength region, which represents the eosin emission. These changes are indicative of the reversal of resonance energy transfer and play important roles in discriminating the fluorescence of the cleaved product from that of the substrate, and the quenching mechanism by FRET from quenching by other sources.

As previously mentioned, cleavage of the DNA substrate by DNase I was near completion, whereas HIV-integrase results in only partial cleavage of the DNA substrate. Since the same fluorogenic substrate was utilized, the intensity ratio of the recovered donor fluorescence (i.e., difference spectra) produced by HIV-IN and DNase I was used to determine the extent of DNA cleavage by HIV-IN. The following equation was used to estimate the extent of cleavage by HIV-IN:

$$[DNA]_c = \frac{F_t - F_0}{F_\infty - F_0} \times [DNA]_i$$

where $[DNA]_c$ is the concentration of cleaved DNA, $F_t$ is the fluorescence intensity of time, t, $F_\infty$ is the fluorescence intensity obtained in the presence of DNase I, $F_0$ is the initial fluorescence intensity, and $[DNA]_i$ is the initial concentration of DNA. Accordingly, the estimated efficiency of the cleavage reaction is 35% in the presence of $Mg^{2+}$ (FIG. 10).

One of the important features of this fluorescence method is its ability to monitor the data rapidly and continuously. Increases in the data density improve the precision in determining reaction rates required for kinetic analysis. FIG. 11A illustrates the kinetics of a continuous fluorescently monitored DNA cleavage reaction by HIV-IN, performed at 37° C. The time-dependent cleavage was monitored with excitation and emission wavelengths of 460 nm and 510 nm, respectively. The excitation wavelength at 460 nm was selected to minimize the direct excitation of the eosin group; changes in the intensity were monitored at 510 nm to avoid the contribution of the emission intensity by the eosin group. An increase in fluorescence intensity was not observed by the addition of integrase in the presence of 20 mM EDTA, indicating that the substrate was not cleaved.

When the reaction was initiated by the addition of integrase in the presence of 7.5 mM $Mg^{2+}$, a time-dependent increase in fluorescence intensity was observed, indicating the time-dependent cleavage of the substrate. Interestingly, when the cleavage reaction was repeated in the presence of 7.5 mM $Mn^{2+}$, smaller changes in fluorescence intensity were observed. The data in FIG. 11A were intensity normalized to compensate for the fluorescence quenching by $Mn^{2+}$. At the end of a 60 minute reaction, the changes in the donor fluorescence were approximately 3 times greater with $Mg^{2+}$ than with $Mn^{2+}$. As reaction time increased, the differences in enhanced fluorescence intensity became greater. These data indicate that the efficiency of the cleavage reaction was better in the presence of $Mg^{2+}$ than $Mn^{2+}$, in agreement with our previous data observed by radioactive assays (Lee et al., *J. Biol. Chem.*, submitted 1994).

Figure 11B:
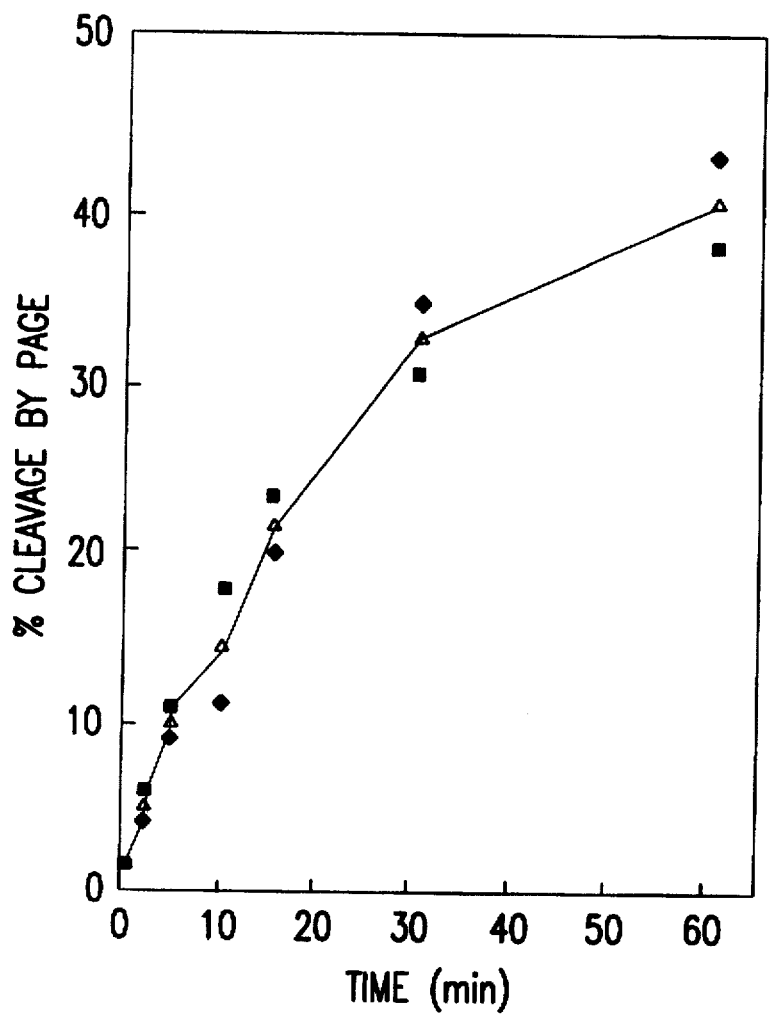

To verify the fluorescent kinetic data, a time-dependent cleavage reaction with the fluorogenic substrate radiolabeled with $^{32}P$ at the 5' end of the F-D1/T1 was performed. The reaction products were analyzed by denaturing PAGE followed by autoradiography and quantified by densitometry. As shown in FIG. 11B, the gel electrophoresis data and the fluorescence data displayed similar patterns of product formation over the same time course, reconfirming the validity of the fluorescence data. The slightly faster kinetics profile in the radioactive assay was attributed to a small variation in substrate concentration between the two experiments.

Confident interpretation of the fluorescence results reported in this Example relies upon the fluorescence quenching being attributed only to FRET. However, it has been previously reported that fluorescence quenching can be observed by both resonance energy transfer (RET) and a mechanism other than RET. The other fluorescence quenching mechanism was observed when single-stranded DNA containing a single fluorophore was annealed to its unmodified complementary strand (Lee et al., *Anal. Biochem.* 220:377–383 (1994); Clegg et al., *Biochemistry* 31:4846–4856 (1992); Cooper and Hagerman, *Biochemistry* 29:9261–9268 (1990)). This mechanism was discussed in Example 1. This quenching is believed to be due to interactions between the probe and the base of the nucleotide. The fluorescence quenching was also accompanied by a spectral shift. Previous time-resolved studies indicate that the recovered lifetimes were 4.2, 2.7, and 0.5 ns. The spectral shift was associated with the quenching of the 4.2 ns decay component (Lee et al., *Anal. Biochem.* 220:377–383 (1994)). In these previous studies, the fluorophore was introduced to DNA via Aminolink 2, which uses a six carbon linker arm.

In the present Example, however, the donor fluorophore was introduced to the DNA via the nucleotide analog, 5-amino(12)-2'-deoxyuridine β-cyanoethyl phosphoramidite, which uses a twelve carbon linker arm instead of a six carbon linker arm. Changes in fluorescence intensity were not detected when the fluorescein-labeled D1/T1 strand was annealed to its unmodified complementary strand, D3, nor when the resulting substrate was incubated with DNase I. Time-resolved decay measurements indicated that the recovered lifetimes were a 4.0 ns decay component and a small fraction of a 0.7 ns component. The lifetimes of both the single (F-D1/T1) and double stranded (substrate 2) fluorogenic substrates were the same. This confirms the absence of fluorescence quenching due to probe-DNA interactions. Therefore, the donor fluorescence quenching observed in this Example can be attributed to FRET. This finding, together with $Mg^{2+}$-dependent endonuclease activity of HIV-IN, made it possible to utilize FRET in a rapid and continuous enzymatic assay system, which will facilitate large-scale screening of integrase inhibitors.

The advantages of this fluorescence assay over other assays include its speed, continuity of reaction monitoring, sensitivity, specificity, and capacity for automation through a 96-well fluorescence microplate reader. Variants of this assay are feasible in both cleavage and synthetic reactions, allowing a wider range of future development for FRET based assays in other enzyme systems.

EXAMPLE 3

Fluorometric Assay for Detecting Nucleic Acid Cleavage Occurring During Catalytic Hybridization Amplification (CHA)

"Catalytic hybridization amplification" (CHA), alternatively known as "cycling probe technology," is described in published PCT application WO 89/09284, and U.S. Pat. Nos. 5,011,769 and 4,876,187. Briefly, CHA is an improved hybridization assay method whereby the target sequence to be detected is able to capture many molecules of the probe in a repeating series of reactions (i.e., "cycling probe"). Essentially, enzyme mediated cleavage of the probe within the probe target duplex results in release of the intact target sequence, which can repeatedly recycle through the reaction pathway. The target sequence serves as a catalytic cofactor for the cleavage of a complementary, labeled nucleic acid probe that is hybridized to the target. The detectable signal in this reaction results from cleavage of the probe, e.g., after repeated CHA cycles, one measures the labeled probe cleavage product. The CHA method is useful in detecting specific DNA or RNA sequences.

The present inventors have reasoned that the last step of CHA (i.e., measuring the labeled probe cleavage product), could be more expeditiously and efficiently carried out by employing the presently disclosed fluorometric assay, based on FRET, for detecting DNA cleavage.

It is expected that the high efficiency of FRET will provide a means to amplify the detection signal. For example, if the donor fluorescence is quenched to 10% of its initial intensity, then complete cleavage of the oligonucleotide substrate (probe) by the RNase H enzyme used in CHA, will result in a 10 fold amplification of the signal. Moreover, only 10% cleavage of the probe will still result in a two fold increase in the detection signal. This intrinsic signal amplification will provide an excellent tool to improve signal-to-noise ratio and thereby increase the confidence in data interpretation.

The cycling probes used consist of DNA-RNA-DNA strands. The first fluorescent probe contains a fluorescein labeled nucleotide positioned at one end of the DNA strand and an $NH_2$-modified nucleotide positioned on the opposite DNA strand. The second fluorescent probe acts as an energy acceptor, and is labeled with at least two fluorophores (eosin and tetramethylrhodamine). The positions of the modified nucleotides will be systematically varied.

The efficiency of FRET of these probes are determined using DNase I and RNase H. Preferably, the flurophores are placed in close proximity of one another, however, modifications closer to the RNA region may have an effect on RNase cleavage of the probe.

By utilizing the target and the selected probe, and varying the concentrations of the target and the probe, the actual sensitivity of the fluorescence signal will be assessed.

All publications and patents mentioned in this specification are indicative of the level of skill of those skilled in the art to which this invention pertains. All publications and patents are herein incorporated by reference to the same extent as if each individual publication or patent was specifically and individually indicated to be incorporated by reference.

Having now fully described this invention, it will be understood by those of skill in the art that the same can be performed within a wide and equivalent range of conditions, formulations, and other parameters without affecting the spirit or scope of the invention or of any embodiment therein.

---

What is claimed is:

1. A method of detecting continuously an endonuclease-mediated nucleic acid cleavage reaction in a fluorometric assay comprising the steps of:

(a) preparing a fluorescently labeled oligonucleotide containing a double-stranded nucleic acid sequence recognizable by said endonuclease, wherein said oligonucleotide acts as a substrate for said endonuclease;

(b) contacting said oligonucleotide of step (a) with said endonuclease in an amount sufficient to cleave said oligonucleotide to produce oligonucleotide products; and (c) detecting continuously a nucleic acid cleavage reaction by detecting an increase in fluorescence intensity.

2. The method of claim 1, wherein said oligonucleotide is fluorescently labeled at one end.

3. The method of claim 1, wherein said oligonucleotide is fluorescently labeled at both ends.

4. The method of claim 1, wherein said nucleic acid is DNA.

5. The method of claim 1, wherein said endonuclease is a restriction endonuclease.

6. The method of claim 1, wherein said endonuclease is a DNase or RNase enzyme.

7. The method of claim 1, wherein said endonuclease is a retroviral integrase enzyme.

8. The method of claim 2, wherein said endonuclease is a restriction endonuclease.

9. The method of claim 3, wherein said endonuclease is a retroviral integrase enzyme.

10. The method of claim 5, wherein said restriction endonuclease is BamHI.

11. The method of claim 7, wherein said retroviral integrase enzyme is HIV integrase.

12. The method of claim 1, wherein said endonuclease-mediated nucleic acid cleavage reaction occurs during a process for amplifying or detecting a specific DNA or RNA sequence.

13. The method of claim 12, wherein said process for amplifying or detecting a DNA or RNA sequence is catalytic hybridization amplification.

14. The method of claim 13, wherein said endonuclease is RNase H.

15. The method of claim 14, wherein said oligonucleotide is fluorescently labeled at both ends.

* * * * *

UNITED STATES PATENT AND TRADEMARK OFFICE
CERTIFICATE OF CORRECTION

PATENT NO. : 5,763,181
DATED : June 9, 1998
INVENTOR(S) : Kenneth J. Livak, et. al.

It is certified that error appears in the above-identified patent and that said Letters Patent is hereby corrected as shown below:

Title page, item [56], insert --

| U.S. PATENT DOCUMENTS | | |
|---|---|---|
| DOCUMENT NUMBER | DATE | NAME |
| 5,723,591 | 03/3/98 | Livak et al. |
| 5,538,848 | 07/23/96 | Livak et al. |

Signed and Sealed this

Ninth Day of February, 1999

Attest:

Attesting Officer

*Acting Commissioner of Patents and Trademarks*